United States Patent [19]

Naka et al.

[11] Patent Number: 4,912,104
[45] Date of Patent: Mar. 27, 1990

[54] TRICYCLIC FUSED PRYIMIDINE DERIVATIVES, AND THEIR USE AS PHARMACEUTICALS

[75] Inventors: Takehiko Naka; Taketoshi Saijo, both of Hyogo; Hiroshi Satoh, Osaka, all of Japan

[73] Assignee: Takeda Chemical Industries, Ltd., Osaka, Japan

[21] Appl. No.: 233,080

[22] Filed: Aug. 16, 1988

[30] Foreign Application Priority Data

Aug. 31, 1987 [JP] Japan .................. 62-218964
May 27, 1988 [JP] Japan .................. 63-130969

[51] Int. Cl.[4] .................. A61K 31/505; C07D 487/14
[52] U.S. Cl. .................. 514/220; 514/267; 540/498; 540/548; 544/251
[58] Field of Search .................. 544/251; 514/267, 211, 514/220; 540/498, 548

[56] References Cited

U.S. PATENT DOCUMENTS 3,637,684  6/1972  Goldman .................. 544/251 X
3,810,894  5/1974  Kranz et al. .................. 544/251 X
4,603,203  7/1986  Furukawa et al. .................. 544/262

FOREIGN PATENT DOCUMENTS 1086707  8/1960  Fed. Rep. of Germany ...... 544/251
2609397  9/1976  Fed. Rep. of Germany ...... 544/251
53-31694  3/1978  Japan .

OTHER PUBLICATIONS

Golec, et al., Chemical Abstracts, vol. 109(3): 22928e (1988).

Primary Examiner—Mukund J. Shah
Assistant Examiner—Diana G. Rivers
Attorney, Agent, or Firm—Wegner & Bretschneider

[57] ABSTRACT

Novel tricyclic fused pyrimidine derivatives represented by the formula (I):

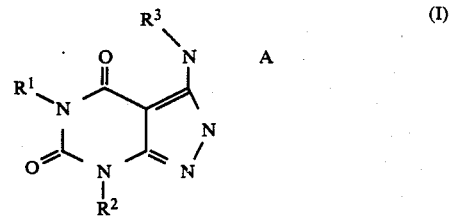

wherein
$R^1$ and $R^2$ are independently $C_{1-8}$ alkyl or $C_{2-8}$ alkenyl;
$R^3$ is hydrogen, $C_{1-3}$ alkyl, $C_{2-3}$ alkenyl, $C_{1-6}$ alkyl-CO-, optionally substituted benzoyl, $C_{1-4}$ alkyl-O-CO-, carbamoyl or formyl; and
A is $C_{2-4}$ alkylene or $C_{2-4}$ alkenylene which may be substituted with $C_{1-3}$ alkyl, halogen, nitro, amino, oxo, or phenyl optionally substituted with 1 to 2 members selected from the class consisting of amino, nitro, hydroxy, methoxy and methyl, and a salt thereof are useful for antiinflammatory, analgesic, antipyretic, anti-allergic anti-psoriatic and liver-protecting agent.

22 Claims, No Drawings

TRICYCLIC FUSED PRYIMIDINE DERIVATIVES, AND THEIR USE AS PHARMACEUTICALS

BACKGROUND OF THE INVENTION

This invention relates to novel tricyclic fused pyrimidine derivatives useful as medicines.

Patent applications directed to pyrazolo[3,4-d]pyrimidine derivatives having, among others, analgesic, antiinflammatory and diuretic actions [cf. Japanese Unexamined Patent Publication No. 53-31694, Japanese Unexamined Patent Publication No. 61-5082 which corresponds to European Patent Publication No. 0166054, etc.] have been made, but the instant tricyclic fused pyrimidine derivatives are novel compounds whose heterocyclic skeleton itself is not known up to now.

The present invention provides tricyclic fused pyrimidine derivatives having analgesic, antiinflammatory, anti-allergic, anti-psoriatic and liver-protecting activities and having a novel skeleton.

DETAILED DESCRIPTION

The present invention relates to a compound represented by the general formula (I):

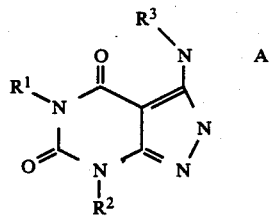

wherein $R^1$ and $R^2$ each stand for an aliphatic hydrocarbon group, $R^3$ stands for hydrogen, an aliphatic hydrocarbon group or acyl group, and A stands for an optionally substituted divalent hydrocarbon chain having 2 to 4 carbon atoms and a salt thereof.

Referring to the above-mentioned general formula (I), examples of the aliphatic hydrocarbon group shown by $R^1$ or $R^2$ include alkyl groups having about 1 to 8 carbon atoms (e.g. methyl, ethyl, propyl, i-propyl, butyl, i-butyl, pentyl, i-pentyl, hexyl, heptyl, octyl, etc.), and alkenyl groups having about 2 to 8 carbon atoms (e.g. vinyl, allyl, 1-propenyl, isopropenyl, 2-butenyl, 1,3-butadienyl, 2-pentenyl, 1-hexenyl, 1-heptenyl, 1-octenyl, etc.), etc. Among them, aliphatic hydrocarbon groups having about 2 to 5 carbon atoms are preferable, especially alkyl groups having about 2 to 5 carbon atoms are preferable.

Examples of the aliphatic hydrocarbon groups shown by $R^3$ include alkyl groups having about 1 to 3 carbon atoms (e.g. methyl, ethyl, propyl, i-propyl), and alkenyl groups having about 2 to 3 carbon atoms (e.g. vinyl, allyl, 1-propenyl, isopropenyl), and, among them, alkyl groups having about 1 to 3 carbon atoms are preferable.

Acyl groups shown by $R^3$ include those derived from organic acids, for example, alkanoyl groups, especially those having 7 or less carbon atoms (e.g. acetyl, trifluoroacetyl, propionyl, butyryl, valeryl, cyclohexanecarbonyl, etc.), aromatic carbonyl groups (e.g. optionally substituted benzoyl, etc.), alkoxycarbonyl groups, especially those, the carbon number of the alkyl moiety of which ranges from about 1 to 4 (e.g. methoxycarbonyl, ethoxycarbonyl, propoxycarbonyl, etc.), carbamoy, formyl, etc. Among them, alkanoyl groups having 7 or less carbon atoms or alkoxycarbonyl group, the carbon number of the alkyl moiety of which ranges from about 1 to 4 are preferable, especially acetyl, propionyl and methoxycarbonyl being preferable.

Examples of divalent hydrocarbon chain having 2 to 4 carbon atoms shown by A include alkylene (e.g. ethylene, trimethylene, tetramethylene), alkenylene (e.g. vinylene, propenylene, etc.).

The hydrocarbon chain may optionally be substituted. Examples of the substituents include, for example, aliphatic hydrocarbon groups, especially alkyl groups having about 1 to 3 carbon atoms (e.g. methyl, ethyl, propyl, isopropyl, etc.), optionally substituted aromatic hydrocarbon groups (e.g. phenyl optionally substituted with 1 to 2 amino, nitro, hydroxy, methoxy, methyl, etc. at ortho-, meta- or para- position, etc.), halogen (e.g. F, cl, Br, etc.), nitro, amino, oxo, etc.

Preferable examples of the optionally substituted divalent hydrocarbon chain having 2 to 4 carbon atoms shown by the above-mentioned A include hydrocarbon chain represented by the formula:

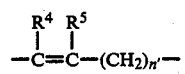

wherein $R^4$ and $R^5$ each stand for hydrogen, an aliphatic hydrocarbon group, an optionally substituted aromatic hydro-carbon group or halogen, and n' denotes an integer of 0 to 2, or an hydrocarbon chain represented by the formula:

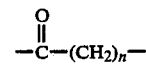

wherein n denotes an integer of 1 to 3, among them, ethylene, oxoethylene

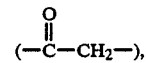

vinylene being preferable.

Reaction (a)

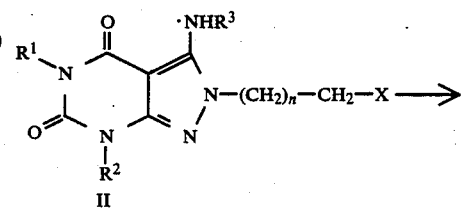

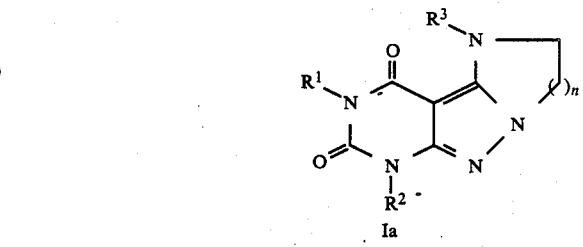

Among the above-mentioned compounds, compounds (I) wherein $R^1$ and $R^2$ each stand for an alkyl group having 3 to 5 carbon atoms, $R^3$ stands for hydrogen, acetyl, propionyl or methoxycarbonyl and A stands for ethylene or vinylene are further preferable.

Examples of the salts of compound (I), include pharmacologically acceptable ones, i.e. acid addition salts such as inorganic acid salts e.g. hydrochloride, hydrobromide, sulfate, nitrate, phosphate, etc., organic acid salts such as acetate, tartrate, citrate, fumarate, maleate, etc.

Production Method:

The above-mentioned compounds of the general formula (I) can be produced by, for example, methods shown below.

$$(-\overset{O}{\underset{}{C}}-CH_2-),$$

wherein $R^1$, $R^2$ and $R^3$ are of the same meaning as defined above, X stands for halogen, and n denotes an integer of 1 to 3.

Reaction (b)

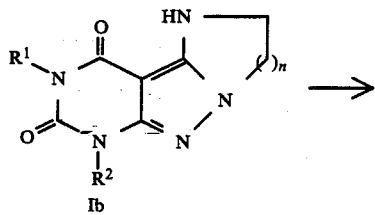
Ib

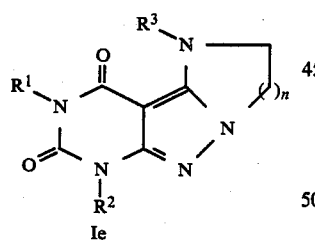
Ie wherein $R^1$, $R^2$, $R^3$ and n are of the same meaning as defined above, provided that $R^3$ is not hydrogen.

Reaction (c)

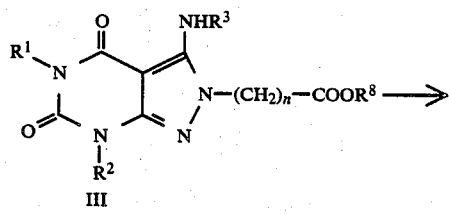
III

-continued
Reaction (c)

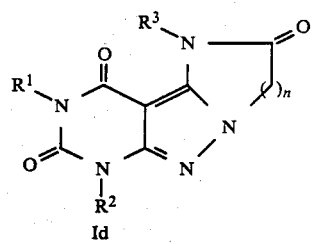
Id wherein $R^1$, $R^2$, $R^3$ and n are of the same meaning as defined above, and $R^8$ stands for a lower alkyl group.

Reaction (d)

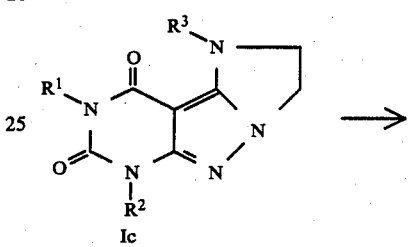
Ic

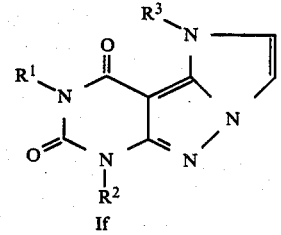
If wherein $R^1$, $R^2$ and $R^3$ are of the same meaning as defined above.

Reaction (e)

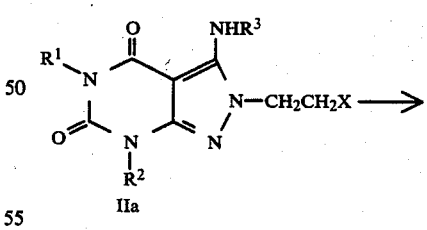
IIa

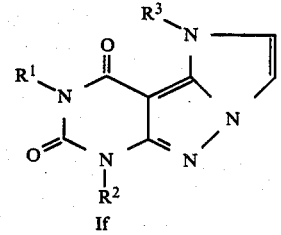
If wherein $R^1$, $R^2$, $R^3$ and X are of the same meaning as defined above.

Reaction (f)

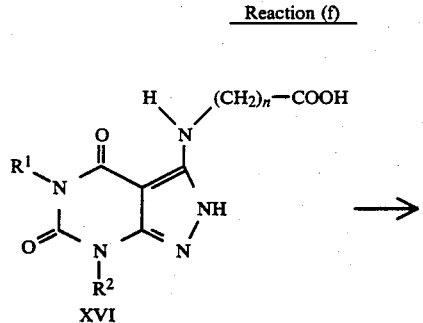

XVI

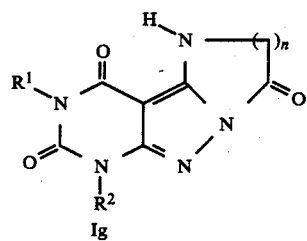

Ig

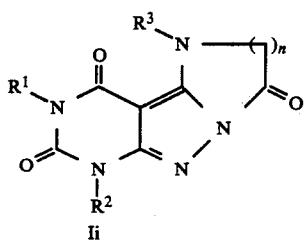

Ii wherein R¹, R², R³ and n are of the same meaning as defined above, provided that R³ is not hydrogen.

Reaction (g)

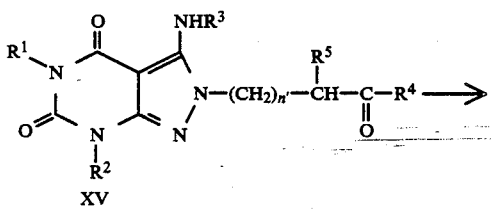

XV

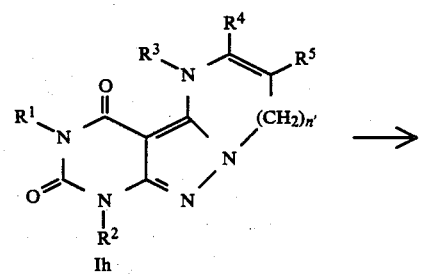

Ih

-continued
Reaction (g)

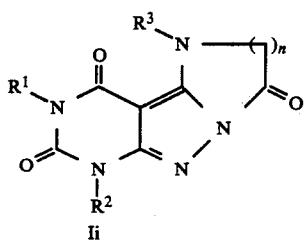

Ij wherein R¹, R², R³, R⁴, R⁵ and X are of the same meaning as defined above, and n' denotes an integer of 0 to 2.

The above-mentioned reaction (a) is a ring-closure reaction in the presence of a base, and the amount of the base is in a range of from 1 to 3 mol. relative to 1 mol. of compound (II). As the base, there may be used sodium hydride, potassium tert-butoxide, potassium carbonate, sodium carbonate, etc. As the solvent, use is made of a polar aprotic solvent such as dimethyl formamide, dimethyl acetamide, dimethyl sulfoxide, acetonitrile, etc. The reaction is carried out preferably at 0° C. to 100° C. for 0.5 to 30 hours. When a strong base such as sodium hydroxide or t-butoxy-potassium is used, the reaction is carried out preferably under ice-cooling by adding such a base as above mentioned in portions. The reaction can be advantageously conducted by adding portionwise a solution of the compound (II) in a solvent such as dimethylformamide to a suspension of a strong base such as sodium hydride in the same solvent under cooling with an ice-bath. It is preferable to raise the reaction temperature up to about room temperature, after the addition of a base in such a manner as above, and to allow the reaction to proceed for further 1 to 2 hours. When the reaction is conducted in the presence of a weak base such as potassium carbonate or sodium carbonate, it is preferable to allow the compound (II) to react with the base above-mentioned in dimethylformamide (DMF) at 50° C. to 130° C. for 10 hours to 30 hours. The desired reaction product can be easily isolated and purified by evaporating the solvent, pouring the residue into ice-water to precipitate crystals, then by recrystallizing from e.g. aqueous alcohol or the like. Depending on cases, a conventional isolation and purification step such as column chromatography can be resorted to.

The reaction (b) involves the alkylation or acylation of the compound (Ib) to yield the compound (Ie). As an alkylating agent, there may be used an alkyl halogenide (e.g. methyl iodide, ethyl iodide, propyl iodide, benzyl bromide, etc.), and as an acylating agent, use is made of an acid anhydride (e.g. acetic anhydride, propionic anhydride, butyric anhydride, etc.) or an acid halogenide (e.g. acetyl chloride, propionyl chloride, butyryl chloride, etc.). And, when the compound (I b) is subjected to alkoxycarbonylation, an alkyl halogenocarbonate (e.g. methyl chlorocarbonate, ethyl chlorocarbonate, etc.) is employed. These reagents are used in an excess amount of about 1 to 5 mol. relative to 1 mol. of the compound (I b), and the reaction is allowed to proceed in the presence of a suitable base. As the base, there may be used potassium carbonate, sodium carbonate, triethylamine, pyridine, etc., and, depending on cases, the reaction is conducted by the addition of a catalytic amount of dimethyl aminopyridine. As the solvent, there may be used pyridine, dimethylformamide, dimethylacetamide, acetonitrile, dioxane, etc., and the reaction is allowed to proceed preferably at 0° C. to 100° C. for 1 to 50 hours. The alkylation is conducted preferably using about 1 to 2 mol. of an alkyl halogenide in dimethylformamide at room temperature to 50° C. for 5 to 20 hours. And, the acylation is conducted preferably using about 1 to 3 mol. of an acid anhydride in pyridine at 50° C. to 100° C. for 5 to 20 hours. Depending on cases, the reaction can be conducted advantageously by adding a catalytic amount of 4-dimethylaminopyridine.

The alkoxycarbonylation is desirably carried out in a solvent such as dioxane, etc., in the presence of a base such as triethylamine, etc. The reaction with alkyl halogenocarbonate is carried out advantageously at room temperature to 60° C. for 5 to 20 hours. The reaction product can be isolated as crystals easily by evaporating the reaction solvent, and then by pouring the residue into ice-water, or by employing a conventional isolation and purification means.

The reaction (c) is a lactam-ring formation reaction in the presence of a base and the base is used in quantities of about 1 to 3 mol. relative to 1 mol. of the compound (III). As preferable bases, there may be used sodium methoxide, sodium ethoxide, etc. As preferable solvents, there may be used alcohol solvents such as methanol, ethanol, etc. The reaction is conducted preferably at 0° C. to 50° C. for 30 minutes to 2 hours. After completion of the reaction, the solvent is distilled off, and the residue is dissolved in water, followed by neutralization with about 1N to 2N-hydrochloric acid to obtain the desired product as crystals.

The reaction (d) is conducted to obtain the compound (I f) by dehydrogenation, and the reaction is carried out in a conventional organic solvent, such as dimethylformamide, dimethylacetamide, acetonitrile, dioxane, toluene, benzene, chloroform, and methylene chloride at 50° to 150° C. for about 5 to 60 hours. The reaction can also be conducted in the presence of benzoyl peroxide, 2,3-dichloro-5,6-dicyano-1,4-benzoquinone (DDQ), selenium dioxide, manganese dioxide, etc., or in the presence of a base such as potassium carbonate or sodium carbonate, and it is especially preferable to conduct the reaction, using as an oxidant 1 to 2 mol. of benzoyl peroxide, in an aprotic solvent such as chloroform under reflux by heating for 5 to 15 hours.

The reaction (e) is a method of obtaining the compound (i f) directly from the compound (II a). The reaction can be carried out analogously to the case of the reaction (a). In the case of the reaction (e), there may be used potassium carbonate or sodium carbonate as a base and dimethylformamide, dimethylacetamide as a solvent. The reaction can be carried out preferably by heating at 80° to 120° C. for 20 to 40 hours. The desired products obtained by the reaction (d) and the reaction (e) can be isolated as crystals easily by, after evaporation of the reaction solvent, pouring the residue into water, followed by subjecting the reaction product to a conventional isolation and purification means such as column chromatography, etc.

The reaction (f) yields the compound (I i) by subjecting the compound (XVI) to the reaction in the presence of a dehydrating agent to give the compound (I g), then by subjecting, when desired, to acylation or alkylation like in the case of the reaction (b). The dehydrating agent employed in the conversion compound (XVI) to the compound (I g) is exemplified by dicyclohexyl carbodiimide (DCC), carbonyl diimidazole (CDI), etc. or a chlorinating agent such as thionyl chloride, phosphorus oxychloride, etc. It is preferable to use about 1 to 10 equivalents of a dehydrating agent relative to the compound (XVI) in such a solvent as methylene chloride, chloroform, benzene, etc. and to allow the reaction to proceed at room temperature to 100° C. for about 1 to 10 hours. It is especially preferable to conduct the reaction in a solvent such as chloroform or methylene chloride, using about 5 to 10 equivalents of thionyl chloride, for about 1 to 5 hours by heating under reflux.

The reaction (g) comprises the dehydration of the compound (XV) under acid or basic conditions to give the desired compound (I h), and the reduction of the compound (I h) to yield the compound (I j). In the reaction of leading the compound (XV) to the compound (I j), as an acid, use is made of an organic or inorganic acid such as p-toluenesulfonic acid, hydrochloric acid, sulfuric acid, etc., and, as a base, use is made of tri-ethylamine, potassium carbonate, sodium carbonate, sodium hydroxide in an amount ranging from catalytic amount to about 2 equivalents relative to the compound (XV), and, as a solvent, use is made of benzene, toluene, xylene, methyl ethyl ketone, etc., and the reaction is allowed to proceed at room temperature to 150° C. for about 5 hours to 3 days. Especially, it is preferable to conduct the reaction in a solvent such as benzene or toluene, etc., using a catalytic amount of p-toluenesulfonic acid, by heating under reflux for about 10 to 20 hours. The hydrogenation of the compound (I h) to the compound (I j) is carried out preferably in a conventional organic solvent such as methanol, ethanol, chloroform, dichloromethane, benzene, acetic acid, etc., under hydrogen atmosphere of normal to 5 atmospheric pressure in the presence of a suitable catalyst, at room temperature to 50° C. for 1 to 10 hours. As the catalyst, Raney nickel, palladium-carbon, platinum-carbon, platinum oxide or rhodium catalyst, etc. are available.

The desired products obtained by the reactions (f) and (g) can be isolated easily as crystals, after distilling off the reaction solvent, by a conventional isolation and purification means.

Among these compounds, the starting compounds (II), (III), (XV) and (XVI) are novel ones, which can be synthesized by the following methods. Starting with the compounds (IV) and (XI) prepared by the methods described in Chem. Ber., 95, 1597 (1962) and Ann. Chem., 691, 142(1966), the key compound (II) can be obtained by the methods described in Chem. Pharm. Bull., 27, 1328(1978) and Chem. Pharm. Bull., 27, 1965(1978) or Japanese Unexamined Patent Publication Nos. 53-31694 and 61-5082. More specifically, the 3-amino derivative (IX) obtained by four processes shown by the reaction (h), (i), (j) and (k) is allowed to react with various alkyl dihalides (e.g. 1-bromo-2-chloroethane, 1-bromo-3-chloropropane, 1-bromo-4-chlorobutane, etc.) as shown by the reaction (1) in an aprotic solvent such as dimethylformamide in the presence of potassium carbonate, sodium carbonate, etc. at 50° to 120° C. for about 10 to 20 hours to obtain the key compound (II). On the other hand, the starting compound (III) can be obtained, as shown by the reaction formula (m), by allowing a compound (IX) to react with a halogenated aliphatic alkyl ester (e.g. bromoacetic acid methyl ester, bromoacetic acid ethyl ester, etc.), in the presence of potassium carbonate or sodium carbonate, in an aprotic solvent such as dimethylformamide, etc. at room temperature to 80° C. for about 1 to 5 hours.

The starting compound (XVI) can be obtained by subjecting the compound (VIII b) prepared by the reaction (i) to alkaline hydrolysis as shown by the reaction (o).

The starting compound (XV) can be prepared, as shown by the reaction (n), by allowing the above-mentioned 3-amino derivative (IX) to react with a haloketone (e.g. bromoacetone, chloroacetone, 3-chloro-2-butanone, phenacyl chloride, phenacyl bromide, etc.) in the presence of potassium carbonate, sodium carbonate, triethylamine, etc., as a base and potassium iodide as a catalyst at room temperature to 50° C. for about 1 to 4 days.

Reaction (h)

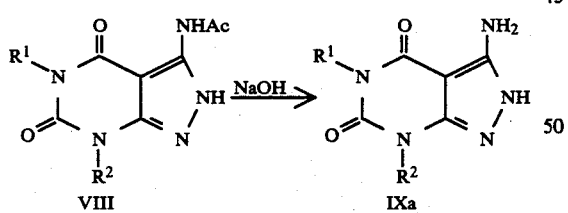

wherein $R^1$, $R^2$ and X are of the same meaning as defined above.

Reaction (i)

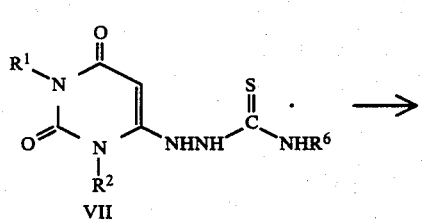

Reaction (i) -continued

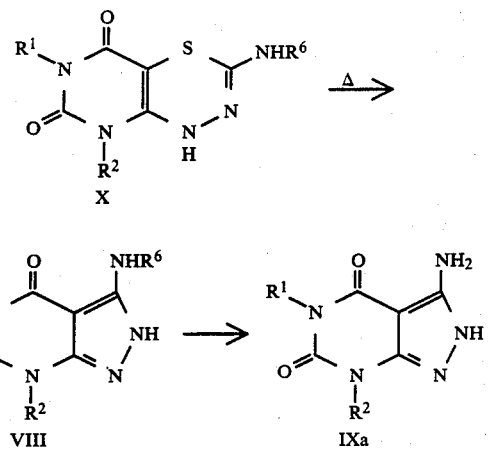

wherein $R^1$ and $R^2$ are of the same meaning as defined above; $R^6$ stands for a lower alkyl group, an acyl group (acetyl, benzoyl, etc.) or a group represented by the formula: $-(CH_2)_nCOOR^7$ (wherein n is of the same meaning as defined above, and $R^7$ stands for a lower alkyl group).

Reaction (j)

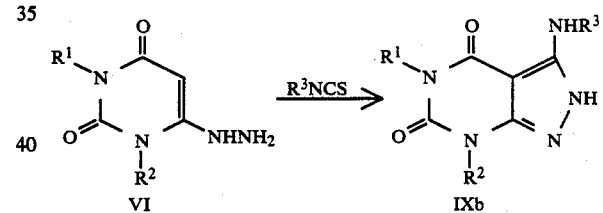

wherein $R^1$, $R^2$ and $R^3$ are of the same meaning as defined above, provided that $R^3$ is not hydrogen.

Reaction (k)

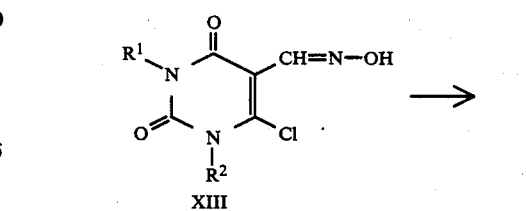

-continued

Reaction (k)

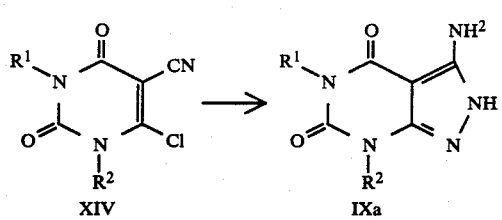

wherein $R^1$ and $R^2$ are of the same meaning as defined above, provided that $R^1=R^2$.

Reaction (l)

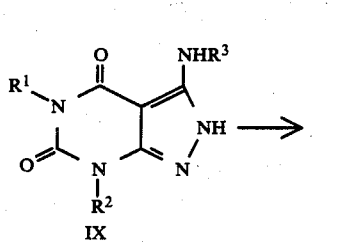

wherein $R^1$, $R^2$, $R^3$, X and n are of the same meaning as defined above.

Reaction (m)

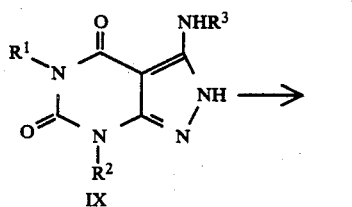

wherein $R^1$, $R^2$, $R^3$, $R^8$ and n are of the same meaning as defined above.

Reaction (n)

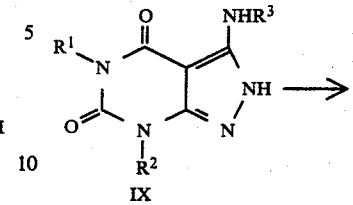

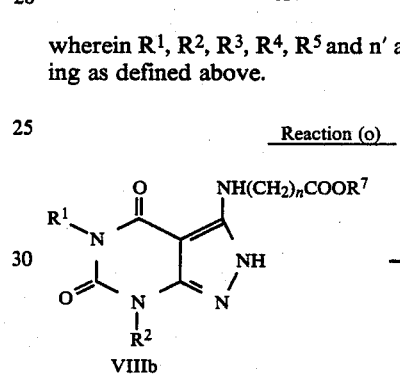

wherein $R^1$, $R^2$, $R^3$, $R^4$, $R^5$ and n' are of the same meaning as defined above.

Reaction (o)

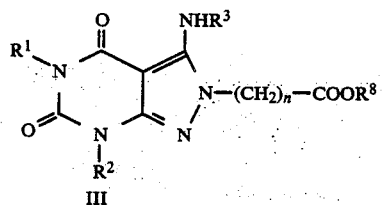

wherein $R^1$, $R^2$, $R^7$ and an are of the same meaning as defined above.

The tricyclic fused pyrimidine derivatives (I) and their salts have antiinflammatory, analgesic, antipyretic, anti-allergic and anti-psoriatic actions on mammals including man, and are useful as ameliorating and therapeutic agents for chronic rheumatoid arthritis, lumbago, neck-shoulder-arm syndrome, psoriasis, etc. The compounds (I) have a liver-protecting action against hepatic injury due to various causes, and they are useful for the therapy of various acute or chronic hepatitis, hepatic injury, fulminant hepatitis, etc., and they are thought to have also a prophylactic action against hepatic fibrosis and cirrhosis.

The compounds (I) are of low-toxicity, and, when they are used as such drugs as mentioned above, they can be safely administered orally or non-orally as such or in admixture with suitable pharmacologically acceptable carriers, excipients or diluents in such dosage form as powders, granules, tablets, capsules, injections, suppositories, ointments, etc. The dose varies with the kinds of disease, symptoms, subjects, routes of administration, etc. In the case of oral administration to, for example, human adults suffering from chronic rheumatoid arthritis or hepatic injury, it is usually preferable to administer the pharmaceutically effective component [compound (I)] in a single dose in the range of about 0.1 mg/kg to 30 mg/kg body weight, preferably about 0.5 mg/kg to 10 mg/kg body weight, once to three times a day.

The following Reference Examples, Working Examples and Experimental Examples will explain the present invention in more practical manner, but it should be noted that these Examples are by no means intended to limit the present invention thereto.

REFERENCE EXAMPLE 1

6-(4-Acetylthiosemicarbazido)-1-butyl-3-propylpyrimidine-2,4(1H,3H)-dione

Acetylisothiocyanate(4.8 g) was added dropwise to a stirred solution of 1-butyl-6-hydrazino-3-propylpyrimidine-2,4(1H,3H)-dione(8.0 g) in dioxane(100 ml). The mixture was stirred for 3 hours at room temperature, then precipitating crystals were collected by filtration. Recrystallization from aqueous alcohol gave colorless crystals (14 g, 94%), m.p. 149°–152° C.

| | Elemental Analysis for $C_{14}H_{23}N_5O_3S$: | | |
|---|---|---|---|
| | C (%) | H (%) | N (%) |
| Calcd.: | 49.25; | 6.79; | 20.51 |
| Found: | 49.31; | 6.70; | 20.48 |

The following compounds were synthesized by the same procedure.

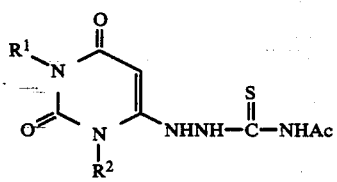

| | | $R^1$ | $R^2$ | mp (°C.) |
|---|---|---|---|---|
| Reference Example | 2 | Et | Et | 202–204 |
| | 3 | Et | Pr | 176–178 |
| | 4 | Et | Bu | 120–127 |
| | 5 | Et | Pen | 111–115 |
| | 6 | Pr | Et | 196–200 |
| | 7 | Pr | All | 140–142 |
| | 8 | Pr | i-Bu | 185–189 |
| | 9 | Pr | Pen | 114–117 |
| | 10 | Bu | Me | 215–217 |
| | 11 | Bu | Et | 210–211 |
| | 12 | Bu | Pr | 155–156 |
| | 13 | Bu | Pen | 105–107 |
| | 14 | Pen | Et | 207–208 |
| | 15 | Pen | Pr | 179–180 |
| | 16 | Pen | All | 172–173 |
| | 17 | Pen | Bu | 142–143 |
| | 18 | Pen | i-Bu | 104–105 |

REFERENCE EXAMPLE 19

3-Acetylamino-7-butyl-5-propylpyrazolo[3,4-d]pyrimidine-4,6(5H,7H)-dione 6-(4-Acetylthiosemicarbazido)-1-butyl-3-propylpyrimidine-2,4(1H,3H)-dione (6.0 g) was heated in dimethylformamide (DMF) (60 ml) at 110°–120° C. for 60 hours. The reaction mixture was concentrated to dryness to give a crystalline product, which were recrystallized from aqueous methanol to afford colorless crystals (4.4 g, 61%),
m.p. 156°–158° C.

| | Elemental Analysis for $C_{14}H_{21}N_5O_3$: | | |
|---|---|---|---|
| | C (%) | H (%) | N (%) |
| Calcd.: | 54.71; | 6.89; | 22.79 |
| Found: | 54.63; | 6.95; | 22.81 |

The following compounds were synthesized by the same procedure.

| | $R^1$ | $R^2$ | mp (°C.) |
|---|---|---|---|
| Reference Example 20 | Et | Et | 254–255 |
| 21 | Et | Pr | 262–264 |
| 22 | Et | Bu | 171–172 |
| 23 | Et | Pen | 152–156 |
| 24 | Pr | Me | 228–230 |
| 25 | Pr | Et | 217–219 |
| 26 | Pr | i-Bu | 177–182 |
| 27 | Pr | Pen | 145–147 |
| 28 | Pr | All | 126–130 |
| 29 | Bu | Me | 229–231 |
| 30 | Bu | Et | 152–153 |
| 31 | Bu | Pr | 133–135 |
| 32 | Bu | Pen | 129–131 |
| 33 | Pen | Et | 145–146 |
| 34 | Pen | All | 130–132 |
| 35 | Pen | Pr | 128–129 |
| 36 | Pen | Bu | 139–141 |
| 37 | Pen | i-Bu | 79–80 |

REFERENCE EXAMPLE 38

3-Amino-7-butyl-5-propylpyrazolo[3,4-d]pyrimidine-4,6-(5H,7H)-dione

3-Acetylamino-7-butyl-5-propylpyrazolo[3,4-d]pyrimidine-4,6(5H,7H)-dione(10 g) was heated under reflux for 5 hours in 80% ethanol(100 ml) containing sodium hydroxide (2 g). The reaction mixture was concentrated to give crystals. The crystals were suspended in water(100 ml), to which was added 6N-HCl to make it weakly acid to afford colorless crystals(8 g,93%),m.p. 209°–211° C.

| | Elemental Analysis for $C_{12}H_{19}N_5O_2$: | | |
|---|---|---|---|
| | C (%) | H (%) | N (%) |
| Calcd.: | 54.32; | 7.22; | 26.40 |
| Found: | 54.66; | 7.20; | 26.38 |

The following compounds were synthesized by the same procedure.

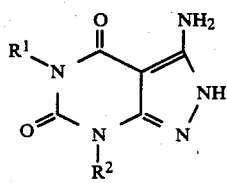

| | R¹ | R² | mp (°C.) |
|---|---|---|---|
| Reference Example 39 | Et | Et | 246–248 |
| 40 | Et | Pr | 236–237 |
| 41 | Et | Bu | 199–200 |
| 42 | Et | Pen | 174–175 |
| 43 | Pr | Me | 235–237 |
| 44 | Pr | Et | 200–202 |
| 45 | Pr | All | 206–208 |
| 46 | Pr | i-Bu | 253–255 |
| 47 | Pr | Pen | 185–187 |
| 48 | Bu | Me | 247–249 |
| 49 | Bu | Et | 167–168 |
| 50 | Bu | Pr | 196–198 |
| 51 | Bu | Pen | 164–165 |
| 52 | Pen | Et | 170–172 |
| 53 | Pen | Pr | 177–178 |
| 54 | Pen | All | 161–162 |
| 55 | Pen | Bu | 181–182 |
| 56 | Pen | i-Bu | 187–188 |

REFERENCE EXAMPLE 57

2-Acetylamino-5-butyl-7-propyl-4H-pyrimido[4,5-e][1,3,4]-thiazine-6,8(5H,7H)-dione To a stirred suspension of N-chlorosuccinimide (2 g) in chloroform was added a solution of 6-(4-acetylthiosemicarbazido)-1-butyl-3-propylpyrimidine-2,4(1H,3H)-dione(3.8 g) in chloroform (20 ml) dropwise under ice-cooling. The mixture was stirred at room temperature for further 3 hours, followed by addition of isopropylether (10 ml) and hexane (10 ml). The mixture was cooled and resulting crystals were collected by filtration and washed with water to afford yellowish brown crystals (3.1 g, 82%), m.p. 165°–167° C.

| Elemental Analysis for $C_{14}H_{21}N_5O_3S$: | | | |
|---|---|---|---|
| | C (%) | H (%) | N (%) |
| Calcd.: | 49.54; | 6.24; | 20.63 |
| Found | 49.49; | 6.29; | 20.55 |

The following compounds were synthesized by the same procedure.

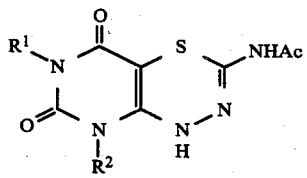

| | R¹ | R² | mp (°C.) |
|---|---|---|---|
| Reference Example 58 | Et | Et | 220–230 |
| 59 | Et | Pr | 127–138 |
| 60 | Et | Bu | 130–140 |
| 61 | Et | Pen | 128–140 |
| 62 | Pr | All | 127–143 |

-continued

| | R¹ | R² | mp (°C.) |
|---|---|---|---|
| 63 | Pr | i-Pen | 143–147 |
| 64 | Pr | Hex | 154–159 |
| 65 | Pr | Hep | 145–150 |
| 66 | Pen | Et | 174–177 |
| 67 | Pen | Pr | 140–145 |
| 68 | Pen | All | 124–127 |
| 69 | Pen | Bu | 144–146 |
| 70 | Pen | i-Bu | 128–130 |
| 71 | Pr | Bu | 165–167 |

REFERENCE EXAMPLE 72

3-Acetylamino-7-butyl-5-propylpyrazo[3,4-d]pyrimidine-4,6(5H,7H)-dione

A mixture of 2-acetylamino-5-butyl-7-propyl-4H-pyrimido[4,5-e][1,3,4]thiadiazine-6,8(5H,7H)-dione(2.8 g) in dioxane (28 ml) was heated at reflux for 1 hr. The reaction mixture was concentrated to dryness, and the concentrate was dissolved in methanol. Insoluble sulfur was filtered off. To the filtrate was added a small quantity of water, and the mixture was cooled to give colorless crystals (2.3 g, 92%), m.p. 156°–158° C.

| Elemental Analysis for $C_{14}H_{21}N_5O_3$: | | | |
|---|---|---|---|
| | C (%) | H (%) | N (%) |
| Calcd.: | 54.71; | 6.89; | 22.79 |
| Found: | 54.70; | 6.93; | 22.81 |

The following compounds were synthesized by the same procedure.

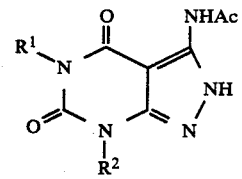

| | R¹ | R² | mp (°C.) |
|---|---|---|---|
| Reference Example 73 | Et | Et | 254–255 |
| 74 | Et | Pr | 262–264 |
| 75 | Et | Bu | 171–172 |
| 76 | Et | Pen | 152–156 |
| 77 | Pr | All | 126–130 |
| 78 | Pr | i-Pen | 136–137 |
| 79 | Pr | Hex | 152–154 |
| 80 | Pr | Bu | 156–158 |
| 81 | Pr | Hep | 159–161 |
| 82 | Pen | Et | 145–146 |
| 83 | Pen | Pr | 128–129 |
| 84 | Pen | All | 130–132 |
| 85 | Pen | Bu | 139–141 |
| 86 | Pen | i-Bu | 79–80 |

REFERENCE EXAMPLE 87

6-Chloro-5-cyano-1,3-diethylpyrimidine-2,4(1H,3H)-dione

To a solution of 1,3-diethylbarbituric acid (61 g) in phosphorus oxychloride (224 ml) was added dimethylformamide (35 ml) with stirring at room temperature and then the reaction solution was refluxed for 3.5 hr. The solution was concentrated to dryness to give an oil. The oil was poured into ice-water to give crystals, 6- chloro-1,3-diethyl-5-formyluracil (64 g), m.p. 88°–89° C.

To a solution of 6-chloro-1,3-diethyl-5-formyluracil (50 g) in ethanl (1l) was added in portions hydroxylamine hydrochloride (50 g) and the mixture was stirred at room temperature for 30 min.

To the reaction mixture was added water(1 l), and resulting precipitates were collected by filtration to obtain 6-chloro-1,3-diethyl-2,4-dioxo-1,2,3,4-tetrahydropyrimidine-5-carbaldehyde oxime (32.5 g), m.p. 115°–116° C.

To a stirred solution of the oxime (16 g) in tetrahydrofuran (320 ml) was added dropwise phosphorus oxychloride (30 g) with stirring. The reaction mixture was concentrated under reduced pressure. To the concentrate was added diisopropylether(200 ml), whereupon 6-chloro-5-cyano-1,3-diethylpyrimidine-2,4(1H,3H)-dione precipitated out as pale yellow prisms(12.4 g), m.p. 92°–94° C.

| Elemental Analysis for $C_9H_{10}N_3O_2Cl$: | | | |
|---|---|---|---|
| | C (%) | H (%) | N (%) |
| Calcd.: | 47.48; | 4.43; | 18.46 |
| Found: | 47.29; | 4.31; | 18.35 |

The following compounds were synthesized by the same procedure.

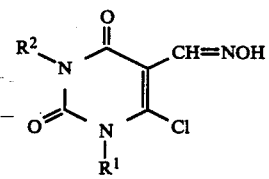

| | $R_1$ | $R^2$ | mp (°C.) |
|---|---|---|---|
| Reference Example 88 | $C_3H_7$ | $C_3H_7$ | 96–99 |
| 89 | i-$C_3H_7$ | i-$C_3H_7$ | 101–103 |
| 90 | $C_4H_9$ | $C_4H_9$ | 94–96 |

Intermediates except for the above(6-chloro-5-formyl compounds, 6-chloro-5-cyano compounds) were hardly crystallizable, and they were used for the succeeding reaction without further purification.

REFERENCE EXAMPLE 91

3-Amino-5,7-diethylpyrazolo[3,4-d]pyrimidine-4,6(5H,7H)-dione

A mixture of 6-chloro-5-cyano-1,3-diethylpyrimidine-2,4(1H, 3H)-dione(5 g) and hydrazine monohydrate (2.2 ml) in methanol (220 ml) was stirred for 10 minutes at room temperature. The reaction mixture was concentrated to dryness under reduced pressure, and the concentrate was crystallized from aqueous methanol to obtain colorless needles(4.3 g), m.p. 246°–248° C.

The following compounds were obtained by the same procedure.

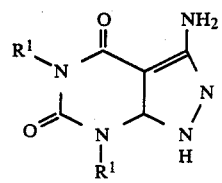

| | $R^1$ | $R^2$ | mp (°C.) |
|---|---|---|---|
| Reference Example 92 | $C_3H_7$ | $C_3H_7$ | 227–229 |
| 93 | i-$C_3H_7$ | i-$C_3H_7$ | 291–295 |
| 94 | $C_4H_9$ | $C_4H_9$ | 192–194 |

REFERENCE EXAMPLE 95

3-Amino-7-butyl-2-(2-chloroethyl)-5-propyl-2H-pyrazolo[3,4-d]pyrimidine-4,6(5H,7H)-dione A mixture of 3-amino-7-butyl-5-propylpyrazolo[3,4-d]pyrimidine-4,6(5H, 7H)-dione(8 g), 1-bromo-2-chloroethane(3.7 ml) and potassium carbonate(6.2 g) in DMF(100 ml) was stirred at 50°–60° C. for 12 hr. The reaction mixture was concentrated to dryness, and the concentrate was extracted with chloroform/water. The chloroform layer was washed with water, dried and concentrated to obtain a brown syrup, which was purified by flash chromatography(silica gel 100 g, chloroform). The purified syrupy product was crystallized from isopropylether to obtain colorless needles(21.5 g, 66%), m.p. 118°–121° C.

| Elemental Analysis for $C_{14}H_{22}N_5O_2Cl$: | | | |
|---|---|---|---|
| | C (%) | H (%) | N (%) |
| Calcd.: | 51.30; | 6.76; | 21.36 |
| Found: | 51.44; | 6.89; | 21.13 |

The following compounds were synthesized by the same procedure.

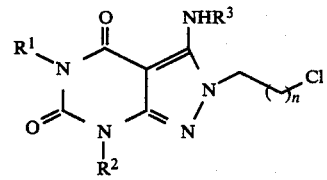

| | $R^1$ | $R^2$ | $R^3$ | n | mp (°C.) |
|---|---|---|---|---|---|
| Reference Example 96 | Et | Et | Me | 1 | 207–210 |
| 97 | Et | Pr | H | 1 | 171–173 |
| 98 | Et | Bu | H | 1 | 144–145 |
| 99 | Et | Pen | H | 1 | 147–149 |
| 100 | Pr | Me | H | 1 | 186–190 |
| 101 | Pr | Et | H | 1 | 123–127 |
| 102 | Pr | All | H | 1 | 120–121 |
| 103 | Pr | Pr | H | 1 | 160–161 |
| 104 | Pr | Bu | H | 1 | 118–121 |
| 105 | Pr | Bu | Me | 1 | 68–73 |
| 106 | Pr | i-Bu | H | 1 | 136–138 |
| 107 | Pr | i-Pen | H | 1 | 144–145 |
| 108 | Pr | Hex | H | 1 | 99–102 |
| 109 | Pr | Hep | H | 1 | 105–106 |
| 110 | Bu | Me | H | 1 | 159–160 |
| 111 | Bu | Et | H | 1 | 120–121 |
| 112 | Bu | Pr | H | 1 | 160–161 |
| 113 | Bu | Bu | H | 1 | 129–132 |

-continued

|     | R¹  | R²   | R³ | n | mp (°C.) |
|-----|-----|------|----|---|----------|
| 114 | Bu  | Pen  | H  | 1 | 118–119  |
| 115 | Pen | Pr   | H  | 1 | 111–112  |
| 116 | Pen | Bu   | H  | 1 | 124–125  |
| 117 | Pen | i-Bu | H  | 1 | 117–118  |
| 118 | Pen | All  | H  | 1 | 118–119  |
| 119 | Pr  | Bu   | Me | 2 | 80–83    |
| 120 | Pr  | Bu   | Me | 3 | 73–76    |

REFERENCE EXAMPLE 121

1-Butyl-6-(4-ethoxycarbonylmethylthiosemicarbazido)-3-propylpyrimidine-2,4(1H,3H)-dione Ethoxycarbonylmethylisothiocyanate (15 g) was added dropwise to a stirred solution of 1-butyl-6-hydrazino-3-propylpyrimidine-2,4(1H,3H)-dione (11 g) in dioxane (100 ml).

The mixture was stirred at room temperature for 3 hours, and the resulting crystals were collected by filtration, followed by washing with a small quantity of dioxane to obtain colorless crystals(18.8 g,96%), m.p. 114°–116° C.

REFERENCE EXAMPLE 122

7-Butyl-3-ethoxycarbonylmethylamino-5-propyl-pyrazolo[3,4-d]pyrimidine-4,6(5H,7H)-dione To a stirred suspension of N-chlorosuccinimide (6.5 g) in chloroform (80 ml) was added in portions 1-butyl-6-(4-ethoxycarbonylmethylthiosemicarbazido)-3-propylpyrimidine-2,4(1H,3H)-dione (18 g) under ice-cooling. The mixture was stirred for one hour, followed by addition of hexane (200 ml) to give an insoluble product. The insoluble product was filtered off.

The filtrate was concentrated to obtain a brown syrup(23 g), which was suspended in dioxane(150 ml). The suspension was heated at 100° C. for one hour. Insoluble material was filtered off, and the filtrate was concentrated. The concentrate was crystallized from ethyl acetate/isopropyl ether to obtain colorless crystals(9.8 g,67%), m.p. 147°–148° C.

REFERENCE EXAMPLE 123

7-Butyl-3-carboxymethylamino-5-propylpyrazolo[3,4-d]pyrimidine-4,6(5H,7H)-dione

To a solution of 7-butyl-3-ethoxycarbonylmethylamino-5-propylpyrazolo[3,4-d]pyrimidine-4,6(5H,7H)-dione(2 g) in ethanol (20 ml) was added a 2N aqueous sodium hydroxide(20 ml), and the mixture was heated at reflux for 1 hr and then concentrated to a half volume and made weakly acid by addition of hydrochloric acid to obtain colorless crystals(1.74 g,95%), m.p. 233°–234° C.(decomp.).

WORKING EXAMPLE 1

6-Butyl-1-methyl-8-propyl-2,3-dihydro-1H-imidazo[2',1':5,1]pyrazolo[3,4-d]pyrimidine-7,9(6H,8H)-dione To a solution of 7-butyl-2-(2-chloroethyl)-3-methylamino-5-propyl-2H-pyrazolo[3,4-d]pyrimidine-4,6(5H,7H)-dione(1.28 g) in DMF(20 ml) was added in portions sodium hydride (60% oil, 0.3%), while stirring under ice-cooling. The reaction mixture was stirred at room temperature for further two hours, then the reaction mixture was concentrated to dryness. The concentrate was added to ice-water, and the mixture was stirred for a while, whereupon crystals precipitated out.

The crystals were collected by filtration, followed by recrystallization from isopropyl ether/hexane to obtain colorless crystals(0.66 g,58%), m.p. 91°–93° C.

| Elemental Analysis for $C_{15}H_{23}N_5O_2$ | | | |
|---|---|---|---|
|        | C(%)  | H(%) | N(%)  |
| Calcd. | 59.00 | 7.59 | 22.93 |
| Found  | 58.88 | 7.63 | 22.96 |

WORKING EXAMPLE 2

6-Butyl-8-propyl-2,3-dihydro-1H-imidazo[2',1':5,1]pyrazolo[3,4-d]pyrimidine-7,9(6H,8H)-dione To a stirred solution of 3-amino-7-butyl-2-(2-chloroethyl)-5-propyl-2H-pyrazolo[3,4-d]pyrimidine-4,6(5H,7H)-dione(3.3 g) in DMF(35 ml) was added in portions sodium hydride (60% oil, 1.2 g) under ice-cooling. The mixture was stirred at room temperature for further two hours, then the reaction mixture was concentrated to dryness. The concentrate was added to ice-water and the mixture was stirred for a while, then crystals precipitated out. The crystals were collected by filtration, followed by recrystallization from aqueous methanol to give colorless crystals(2.2 g,76%), m.p. 170°–172° C.

| Elemental Analysis for $C_{14}H_{21}N_5O_2$ | | | |
|---|---|---|---|
|        | C(%)  | H(%) | N(%)  |
| Calcd. | 57.71 | 7.26 | 24.04 |
| Found  | 57.78 | 7.29 | 24.01 |

WORKING EXAMPLE 3

6,8-Dibutyl-2,3-dihydro-1H-imidazo[2',1':5,1]pyrazolo[3,4-d]pyrimidine-7,9(6H,8H)-dione To a stirred solution of 3-amino-2-(2-chloromethyl)-5,7-dibutyl-2H-pyrazolo[3,4-d]pyrimidine-4,6(5H,7H)-dione(1.2 g) in DMF (20 ml) was added in portions sodium hydride(60% oil, 0.3 g) under ice-cooling. The mixture was stirred at room temperature for further two hours, followed by concentration to dryness. The concentrate was added to ice-water and the mixture was stirred for a while, whereupon crystals precipitated out. The crystals were collected by filtration and recrystallized from methanol/isopropyl ether to give colorless crystals(0.65 g, 50%), m.p. 141°–142° C.

| Elemental Analysis for $C_{15}H_{23}N_5O_2$ | | | |
|---|---|---|---|
|        | C(%)  | H(%) | N(%)  |
| Calcd. | 59.00 | 7.59 | 22.93 |
| Found  | 58.69 | 7.62 | 22.80 |

WORKING EXAMPLE 4

6-Butyl-1,8-dimethyl-2,3-dihydro-1H-imidazo[2',1':5,1]pyrazolo[3,4-d]pyrimidine-7,9(6H,8H)-dione To a stirred solution of 7-butyl-5-methyl-3-methylamino-2H-pyrazolo[3,4-d]pyrimidine-4,6(5H,7H)-dione(1.76 g) in DMF (30 ml) was added in portions sodium hydride(60% oil, 0.67 g) under ice-cooling. The mixture was further stirred at room temperature for two hours, then the reaction mixture was concentrated to dryness. The concentrate was added to ice-water and the mixture was stirred for a while, whereupon crystals precipitated out. Crystals were collected by filtration and recrystallized from acetone/isopropyl ether/hexane to give colorless crystals(0.9 g, 58%), m.p. 166°–168° C.

| Elemental Analysis for $C_{13}H_{19}N_5O_2$ | | | |
|---|---|---|---|
| | C(%) | H(%) | N(%) |
| Calcd. | 56.30 | 6.91 | 25.25 |
| Found | 56.47 | 6.89 | 25.30 |

WORKING EXAMPLE 5

6-Isobutyl-8-propyl-2,3-dihydro-1H-imidazo[2',1':5,1]-pyrazolo[3,4-d]pyrimidine-7,9(6H,8H)-dione To a stirred solution of 3-amino-2-(2-chloroethyl)-7-isobutyl-5-propyl-2H-pyrazolo[3,4-d]pyrimidine-4,6(5H,7H)-dione(2.0 g) in DMF(40 ml) was added in portions sodium hydride (60% oil, 0.49 g) under ice-cooling. The mixture was stirred for two hours at room temperature, then the reaction mixture was concentrated to dryness. The concentrate was added to ice-water and the mixture was stirred for a while, whereupon crystals precipitated out. Crystals were collected by filtration, followed by recrystallization from ethanol/hexane to give colorless crystals(0.91 g, 51%), m.p. 215°–216° C.

| Elemental Analysis for $C_{14}H_{21}N_5O_2$ | | | |
|---|---|---|---|
| | C(%) | H(%) | N(%) |
| Calcd. | 57.71 | 7.26 | 24.04 |
| Found | 57.53 | 7.17 | 24.16 |

WORKING EXAMPLE 6

6-Pentyl-8-propyl-2,3-dihydro-1H-imidazo[2',1':5,1-]pyrazolo[3,4-d]pyrimidine-7,9(6H,8H)-dione To a stirred solution of 3-amino-2-(2-chloroethyl)-7-pentyl-5-propyl-2H-pyrazolo[3,4-d]pyrimidine-4,6(5H,7H)-dione(2.3 g) in DMF(30 ml) was added in portions sodium hydride (60% oil, 0.54 g) under ice-cooling. The mixture was stirred at room temperature for further two hours, then the reaction mixture was concentrated to dryness. The concentrate was added to ice-water and the mixture was stirred for a while, whereupon crystals precipitated out, followed by recrystallization from ethanol/hexane to obtain colorless crystals(1.23 g 60%), m.p. 145°–146° C.

| Elemental Analysis for $C_{15}H_{23}N_5O_2$ | | | |
|---|---|---|---|
| | C(%) | H(%) | N(%) |
| Calcd. | 59.00 | 7.59 | 22.93 |
| Found | 59.02 | 7.62 | 22.94 |

WORKING EXAMPLE 7

6,8-Diethyl-2,3-dihydro-1H-imidazo[2',1':5,1-]pyrazolo[3,4-d]pyrimidine-7,9(6H,8H)-dione To a stirred solution of 3-amino-2-(2-chloroethyl)-5,7-diethyl-2H-pyrazolo[3,4-d]pyrimidine-4,6(5H,7H)-dione(1.0 g) in DMF 20 ml) was added in portions sodium hydride(60% oil, 0.28 g) under ice-cooling. The mixture was stirred at room temperature for further two hours, then the reaction mixture was concentrated to dryness. The concentrate was added to ice-water and the mixture was stirred for a while, whereupon crystals precipitated out. The crystals were collected by filtration, followed by recrystallization from methylene chloride/hexane to obtain colorless crystals(0.48 g, 55%), m.p. 201°–202° C.

| Elemental Analysis for $C_{11}H_{15}N_5O_2$ | | | |
|---|---|---|---|
| | C(%) | H(%) | N(%) |
| Calcd. | 53.00 | 6.07 | 28.10 |
| Found | 53.02 | 6.04 | 28.32 |

WORKING EXAMPLE 8

6,8-Dimethyl-2,3-dihydro-1H-imidazo[2',1':5,1-]pyrazolo[3,4-d]pyrimidine-7,9(6H,8H)-dione To a stirred solution of 3-amino-2-(2-chloroethyl)-5,7-dimethyl-2H-pyrazolo[3,4-d]pyrimidine-4,6(5H,7H)-dione(1.25 g) in DMF (50 ml) was added in portions sodium hydride(60% oil, 0.3 g) under ice-cooling. The mixture was stirred at room temperature for further two hours, then the reaction mixture was concentrated to dryness. The concentrate was added to ice-water and the mixture was stirred for a while, whereupon crystals precipitated out. Crystals were collected by filtration, followed by recrystallization from methylene chloride/methanol to give colorless crystals(0.56 g, 52%), m.p. 267°–268° C.

| Elemental Analysis for $C_{10}H_{13}N_5O_2$ | | | |
|---|---|---|---|
| | C(%) | H(%) | N(%) |
| Calcd. | 48.87 | 5.01 | 31.66 |
| Found | 48.84 | 5.01 | 31.51 |

WORKING EXAMPLE 9

6-Methyl-8-propyl-2,3-dihydro-1H-imidazo[2',1':5,1-]pyrazolo[3,4-d]pyrimidine-7,9(6H,8H)-dione To a stirred solution of 3-amino-2-(2-chloroethyl)-7-methyl-5-propyl-2H-pyrazolo[3,4-d]pyrimidine-4,6(5H,7H)-dione(2.5 g) in DMF(30 ml) was added in portions sodium hydride (60% oil, 0.7 g) under ice-cooling. The mixture was stirred at room temperature for further two hours. The reaction mixture was then concentrated to dryness. The concentrate was added to ice-water and the mixture was stirred for a little while, whereupon crystals precipitated out. Crystals were collected by filtration, followed by recrystallization from aqueous alcohol to obtain colorless crystals(1.3 g, 60%), m.p. 246°–248° C.

| Elemental Analysis for $C_{11}H_{15}N_5O_2$ | | | |
|---|---|---|---|
| | C(%) | H(%) | N(%) |
| Calcd. | 53.00 | 6.07 | 28.10 |
| Found | 52.98 | 6.02 | 28.19 |

WORKING EXAMPLE 10

6-Ethyl-8-propyl-2,3-dihydro-1H-imidazo[2',1':5,1-]pyrazolo[3,4-d]pyrimidine-7,9(6H,8H)-dione To a stirred solution of 3-amino-2-(2-chloroethyl)-7-ethyl-5-propyl-2H-pyrazolo[3,4-d]pyrimidine-4,6(5H,7H)-dione(2.0 g in DMF (25 ml) was added in portions sodium hydride (60% oil, 0.53 g) under ice-cooling. The mixture was stirred at room temperature for further two hours. The reaction mixture was concentrated to dryness. The concentrate was added to ice-water and the mixture was stirred for a little while, whereupon crystals precipitated out. Crystals were collected by filtration, followed by recrystallization from methylene chloride/hexane to obtain colorless crystals(0.98 g, 56%), m.p. 212°–214° C.

| | Elemental Analysis for $C_{12}H_{17}N_5O_2$ | | |
|---|---|---|---|
| | C(%) | H(%) | N(%) |
| Calcd. | 54.74 | 6.51 | 26.60 |
| Found | 54.88 | 6.51 | 26.69 |

WORKING EXAMPLE 11

8-Butyl-6-methyl-2,3-dihydro-1H-imidazo[2',1':5,1-]pyrazolo[3,4-d]pyrimidine-7,9(6H,8H)-dione To a stirred solution of 3-amino-5-butyl-2-(2-chloroethyl)-7-methyl-2H-pyrazolo[3,4-d]pyrimidine-4,6(5H,7H)-dione(2.0 g in DMF(25 ml) was added in portions sodium hydride (60% oil, 0.4 g) under ice-cooling. The mixture was stirred at room temperature for further two hours. The reaction mixture was concentrated to dryness. The concentrate was added to ice-water and the mixture was stirred for a little while, whereupon crystals precipitated out, which were collected by filtration, followed by recrystallization from methylene chloride/hexane to obtain colorless crystals(1.04 g, 51%), m.p. 217°–218° C.

| | Elemental Analysis for $C_{12}H_{17}N_5O_2$ | | |
|---|---|---|---|
| | C(%) | H(%) | H(%) |
| Calcd. | 54.74 | 6.51 | 26.60 |
| Found | 54.55 | 6.51 | 26.38 |

WORKING EXAMPLE 12

8-Butyl-6-ethyl-2,3-dihydro-1H-imidazo[2',1':5,1-]pyrazolo[3,4-d]pyrimidine-7,9(6H,8H)-dione To a stirred solution of 3-amino-5-butyl-2-(2-chloroethyl)-7-ethyl-2H-pyrazolo[3,4-d]pyrimidine-4,6(5H,7H)-dione(2.0 g) in DMF(25 ml) was added in portions sodium hydride (60% oil, 0.4 g) under ice-cooling. The mixture was stirred at room temperature for further two hours. The reaction mixture was concentrated to dryness. The concentrate was added to ice-water and the mixture was stirred for a little while, whereupon crystals precipitated out, which were collected by filtration, followed by recrystallization from methylene chloride/hexane to obtain colorless crystals(1.01 g, 57%), m.p. 162°–163° C.

| | Elemental Analysis for $C_{13}H_{19}N_5O_2$ | | |
|---|---|---|---|
| | C(%) | H(%) | N(%) |
| Calcd. | 56.30 | 6.91 | 25.25 |
| Found | 56.35 | 6.85 | 25.19 |

WORKING EXAMPLE 13

6,8-Dipropyl-2,3-dihydro-1H-imidazo[2'1':5,1-]pyrazolo[3,4-d]pyrimidine-7,9(6H,8H)-dione To a stirred solution of 3-amino-2-(2-chloroethyl)-5,7-dipropyl-2H-pyrazolo[3,4-d]pyrimidine-4,6(5H,7H)-dione (2.5 g) in DMF (25 ml) was added in portions sodium hydride (60% oil, 0.5 g) under ice-cooling. The mixture was stirred at room temperature for further two hours. The reaction mixture was concentrated to dryness. The concentrate was added to ice-water and the mixture was stirred for a little while, whereupon crystals precipitated out, which were collected by filtration, followed by recrystallization from methylene chloride/hexane to obtain colorless crystals(1.08 g,61%), m.p. 207°–209° C.

| | Elemental Analysis for $C_{13}H_{19}N_5O_2$ | | |
|---|---|---|---|
| | C(%) | H(%) | N(%) |
| Calcd. | 56.30 | 6.91 | 25.25 |
| Found | 56.32 | 6.88 | 25.27 |

WORKING EXAMPLE 14

6,8-Dibutyl-1-methyl-2,3-dihydro-1H-imidazo[2',1':5,1]-pyrazolo[3,4-d]pyrimidine-7,9(6H,8H)-dione To a stirred solution of 5,7-dibutyl-2-(2-chloroethyl)-3-methylamino-2H-pyrazolo[3,4-d]pyrimidine-4,6(5H,7H)-dione(5.8 g) in DMF(60 ml) was added in portions sodium hydride (60% oil, 1.3 g) under ice-cooling. The mixture was stirred out room temperature for further two hours. The reaction mixture was concentrated to dryness. The concentrate was added to ice-water and the mixture was stirred for a little while, whereupon crystals precipitated out. Crystals were collected by filtration, followed by recrystallization from isopropyl ether/hexane to obtain colorless crystals (3.2 g, 61%), m.p. 119°–121° C.

| | Elemental Analysis for $C_{16}H_{25}N_5O_2$ | | |
|---|---|---|---|
| | C(%) | H(%) | N(%) |
| Calcd. | 60.17 | 7.89 | 21.93 |
| Found | 60.12 | 7.89 | 21.88 |

WORKING EXAMPLE 15

8-Butyl-6-propyl-2,3-dihydro-1H-imidazo[2',1':5,1-]pyrazolo[3,4-d]pyrimidine-7,9(6H,8H)-dione To a stirred solution of 3-amino-5-butyl-2-(2-chloroethyl)-7-propyl-2H-pyrazolo[3,4-d]pyrimidine-4,6(5H,7H)-dione(2.0 g) in DMF(25 ml) was added in portions sodium hydride (60% oil, 0.4 g) under ice-cooling. The mixture was stirred at room temperature for further two hours. The reaction mixture was concentrated to dryness. The concentrate was added to ice-water and the mixture was stirred for a little while, whereupon crystals precipitated out. Crystals were collected by filtration, followed by recrystallization from methylene chloride/hexane to obtain colorless crystals(1.00 g, 56%), m.p. 148°–150° C.

Elemental Analysis for $C_{14}H_{21}N_5O_2$

|  | C(%) | H(%) | N(%) |
| --- | --- | --- | --- |
| Calcd. | 57.71 | 7.26 | 24.05 |
| Found | 57.63 | 7.25 | 24.02 |

WORKING EXAMPLE 16

8-Butyl-6-pentyl-2,3-dihdyro-1H-imidazo[2',1':5,1-]pyrazolo[3,4-d]pyrimidine-7,9(6H,8H)-dione To a stirred solution of 3-amino-5-butyl-2-(2-chloroethyl)-7-pentyl-2H-Pyrazolo[3,4-d]pyrimidine-4,6(5H,7H)-dione(2.0 g) in DMF(25 ml) was added in portions sodium hydride (60% oil, 0.5 g) under ice-cooling. The mixture was stirred at room temperature for further two hours. The reaction mixture was concentrated to dryness. The concentrate was added to ice-water and the mixture was stirred for a little while, whereupon crystals precipitated out. Crystals were collected by filtration and recrystallized from methylene chloride/hexane to obtain colorless crystals(810 mg, 45%), m.p. 130°-132° C.

Elemental Analysis for $C_{16}H_{25}N_5O_2$

|  | C(%) | H(%) | N(%) |
| --- | --- | --- | --- |
| Calcd. | 60.17 | 7.89 | 21.93 |
| Found | 60.14 | 7.90 | 21.93 |

WORKING EXAMPLE 17

6-Isopentyl-8-propyl-2,3-dihydro-1H-imidazo[2',1':5,1-]pyrazolo[3,4-d]pyrimidine-7.9(6H,8H)-dione To a stirred solution 3-amino-2-(2-chloroethyl)-7-isopentyl-5-propyl-2H-pyrazolo[3,4-d]pyrimidine-4,6(5H,7H)-dione(1.3 g) in DMF(15 ml) was added in portions sodium hydride (60% oil, 0.23 g) under ice-cooling. The mixture was stirred at room temperature for further four hours. The reaction mixture was concentrated to dryness. The concentrate was added to ice-water and the mixture was stirred for a while to give crystals. Crystals were collected by filtration, followed by recrystallization from ethyl acetate/hexane to obtain colorless crystals(0.87 g, 75%), m.p. 185°-187° C.

Elemental Analysis for $C_{15}H_{23}N_5O_2$

|  | C(%) | H(%) | N(%) |
| --- | --- | --- | --- |
| Calcd. | 59.00 | 7.59 | 22.93 |
| Found | 58.75 | 7.55 | 22.70 |

WORKING EXAMPLE 18

6-Allyl-8-propyl-2,3-dihydro-1H-imidazo[2',1':5,1-]pyrazolo[3,4-d]pyrimidine-7,9(6H,8H)-dione To a stirred solution of 7-allyl-3-amino-2-(2-chloroethyl)-5-propyl-2H-pyrazolo[3,4-d]pyrimidine-4,6(5H,7H)-dione(0.85 g) in DMF(10 ml) was added in portions sodium hydride (60%, oil, 0.17 g) under ice-cooling. The mixture was stirred at room temperature for further three hours. The reaction mixture was concentrated to dryness. The concentrate was added to ice-water and the mixture was stirred for a while. Precipitating crystals were collected by filtration, followed by recrystallization from methylene chloride/hexane to obtain colorless crystals(0.35 g, 47%), m.p. 174°-175° C.

Elemental Analysis for $C_{13}H_{17}N_5O_2$

|  | C(%) | H(%) | N(%) |
| --- | --- | --- | --- |
| Calcd. | 56.72 | 6.22 | 25.44 |
| Found | 56.68 | 6.23 | 25.40 |

WORKING EXAMPLE 19

6-Heptyl-8-propyl-2,3-dihydro-1H-imidazo[2',1':5,1-]pyrazolo[3,4-d]pyrimidine-7,9(6H,8H)-dione To a stirred solution of 3-amino-2-(2-chloroethyl)-7-heptyl-5-propyl-2H-pyrazolo[3,4-d]pyrimidine-4,6(5H,7H)-dione(1.93 g) in DMF(20 ml) was added in portions sodium hydride (60% oil, 0.32 g) under ice-cooling. The mixture was stirred at room temperature for further 5 hours. The reaction mixture was concentrated to dryness. The concentrate was added to ice-water and the mixture was stirred for a while, whereupon crystals precipitated out. The crystals were collected by filtration, followed by recrystallization from ethyl acetate/hexane to obtain colorless crystals(1.14 g, 66%), m.p. 133°-134° C.

Elemental Analysis for $C_{17}H_{27}N_5O_2$

|  | C(%) | H(%) | N(%) |
| --- | --- | --- | --- |
| Calcd. | 61.24 | 8.16 | 21.00 |
| Found | 61.32 | 8.24 | 21.05 |

WORKING EXAMPLE 20

6-Hexyl-8-propyl-2,3-dihydro-1H-imidazo[2',1':5,1-]pyrazolo[3,4-d]pyrimidine-7,9(6H,8H)-dione To a stirred solution of 3-amino-2-(2-chloroethyl)-7-hexyl-5-propyl-2H-pyrazolo[3,4-d]pyrimidine-4,6(5H,7H)-dione(1.85 g) in DMF(20 ml) was added in portions sodium hydride (60%, 0.32 g) under ice-cooling. The mixture was stirred at room temperature for 5 hours. The reaction mixture was concentrated to dryness and the residue was added to ice-water, followed by stirring for a while, whereupon crystals precipitated out. The crystals were recrystallized from ethyl acetate/hexane to obtain colorless crystals(0.99 g, 60%), m.p. 129°-130° C.

Elemental Analysis for $C_{16}H_{25}N_5O_2$

|  | C(%) | H(%) | N(%) |
| --- | --- | --- | --- |
| Calcd. | 60.17 | 7.89 | 21.93 |
| Found | 60.19 | 7.93 | 21.94 |

WORKING EXAMPLE 21

6-Ethyl-8-pentyl-2,3-dihydro-1H-imidazo[2',1':5,1-]pyrazolo[3,4-d]pyrimidine-7,9(6H,8H)-dione To a stirred solution of 3amino-2-(2-chloroethyl)-7-ethyl-5-pentyl-2H-pyrazolo[3,4-d]pyrimidine-4,6(5H,7H)-dione(3.0 g) in DMF(40 ml) was added in portions sodium hydride (60% oil, 0.56 g) under ice-cooling. The mixture was stirred at room temperature for 6 hours. The reaction mixture was concentrated to dryness and the residue was added to ice-water, followed by stirring for a while, whereupon crystals precipitated out. The crystals were collected by filtration and recrystallized from methylene chloride/isopropyl ether to obtain colorless crystals(1.8 g, 68%), m.p. 153°–154° C.

| Elemental Analysis for $C_{14}H_{21}N_5O_2$ | | | |
|---|---|---|---|
| | C(%) | H(%) | N(%) |
| Calcd. | 57.71 | 7.26 | 24.04 |
| Found | 57.83 | 7.34 | 24.05 |

WORKING EXAMPLE 22

8-Ethyl-6-propyl-2,3-dihdyro-1H-imidazo[2',1':5,1-]pyrazolo[3,4-d]pyrimidine-7,9(6H,8H)-dione To a stirred solution of 3-amino-2-(2-chloroethyl)-5-ethyl-7-propyl-2H-pyrazolo[3,4-d]pyrimidine-4,6(5H,7H)-dione(2.4 g) in DMF(40 ml) was added in portions sodium hydride (60% oil, 0.49 g) under ice-cooling. The mixture was stirred at room temperature for further 5 hours. The reaction mixture was concentrated to dryness and the residue was added to ice-water, followed by stirring for a while, whereupon crystals precipitated out. The crystals were collected by filtration and recrystallized from methylene chloride/hexane to obtain colorless crystals(1.5 g, 69%), m.p. 183°–184° C.

| Elemental Analysis for $C_{12}H_{17}N_5O_2$ | | | |
|---|---|---|---|
| | C(%) | H(%) | N(%) |
| Calcd. | 54.74 | 6.51 | 26.60 |
| Found | 54.57 | 6.49 | 26.42 |

WORKING EXAMPLE 23

6-Butyl-8-ethyl-2,3-dihydro-1H-imidazo[2',1':5,1-]pyrazolo[3,4-d]pyrimidine-7,9(6H,8H)-dione To a stirred solution of 3-amino-7-butyl-2-(2chloroethyl)-5-ethyl-2H-pyrazolo[3,4-d]pyrimidine-4,6(5H,7H)-dione(2.4 g) in DMF(40 ml) was added in portions sodium hydride (60% oil, 0.47 g) under ice-cooling. The mixture was stirred at room temperature for further 4 hours. The reaction mixture was concentrated to dryness and the residue was added to ice-water, followed by stirring for a while, whereupon crystals precipitated out. The crystals were collected by filtration, followed by recrystallization from methanol/ethyl acetate/isopropyl ether to obtain colorless crystals (1.45 g, 68%), m.p. 168°–170° C.

| Elemental Analysis for $C_{13}H_{19}N_5O_2$ | | | |
|---|---|---|---|
| | C(%) | H(%) | N(%) |
| Calcd. | 56.30 | 6.91 | 25.25 |
| Found | 56.34 | 6.96 | 25.29 |

WORKING EXAMPLE 24

8-Ethyl-6-pentyl-2,3-dihydro-1H-imidazo[2'.1':5,1-]pyrazolo[3,4-d]pyrimidine-7,9(6H,8H)-dione To a stirred solution of 3-amino-2-(2-chloroethyl)-5-ethyl-7-pentyl-2H-pyrazolo[3,4-d]pyrimidine-4,6(5H,7H)-dione(1.6 g) in DMF(20 ml) was added in portions sodium hydride (60% oil, 0.3 g) under ice-cooling. The mixture was stirred at room temperature for further 4 hours, followed by concentration to dryness. The concentrate was then added to ice-water, followed by stirring for a while. Whereupon crystals precipitated out. The crystals were collected by filtration, followed by recrystallization from methylene chloride/hexane to give colorless crystals(1.0 g, 72%), m.p. 150°–151° C.

| Elemental Analysis for $C_{14}H_{21}N_5O_2$ | | | |
|---|---|---|---|
| | C(%) | H(%) | N(%) |
| Calcd. | 57.71 | 7.26 | 24.04 |
| Found | 57.72 | 7.32 | 23.97 |

WORKING EXAMPLE 25

6-Butyl-8-pentyl-2,3-dihydro-1H-imidazo[2',1':5,1-]pyrazolo[3,4-d]pyrimidine-7,9(6H,8H)-dione To a stirred solution of 3-amino-7-butyl-2-(2-chloroethyl)-5-pentyl-2H-pyrazolo[3,4-d]pyrimidine-4,6(5H,7H)-dione(3.5 g) in DMF(80 ml) was added in portions sodium hydride (60% oil, 0.55 g) under ice-cooling. The mixture was stirred at room temperature for further 5 hours. The reaction mixture was concentrated to dryness and added to ice-water. This was followed by stirring for a while, whereupon crystals precipitated out. The crystals were collected by filtration, followed by recrystallization from methylene chloride/hexane to give colorless crystals(2.30 g, 73%), m.p. 124°–125° C.

| Elemental Analysis for $C_{16}H_{25}N_5O_2$ | | | |
|---|---|---|---|
| | C(%) | H(%) | N(%) |
| Calcd. | 60.17 | 7.89 | 21.93 |
| Found | 60.18 | 7.95 | 21.92 |

WORKING EXAMPLE 26

8-Pentyl-6-propyl-2,3-dihydro-1H-imidazo[2',1':5,1-]pyrazolo[3,4-d]pyrimidine-7,9(6H,8H)-dione To a stirred solution of 3-amino-2-(2-chloroethyl)-5-pentyl-7-propyl-2H-pyrazolo[3,4-d]pyridine-4,6(5H,7H)-dione(3.5 g) in DMF(30 ml) was added in portions sodium hydride (60% oil, 0.55 g) under ice-cooling. The mixture was stirred at room temperature for further 5 hours. The reaction mixture was then concentrated to dryness and the residue was added to ice-water. This was followed by stirring for a while, whereupon crystals precipitated out. The crystals were collected by filtration and recrystallized from methylene chloride/hexane to give colorless crystals(2.4 g, 77%), m.p. 156°–157° C.

| Elemental Analysis for $C_{15}H_{23}N_5O_2$ | | | |
|---|---|---|---|
| | C(%) | H(%) | N(%) |
| Calcd. | 59.00 | 7.59 | 22.93 |
| Found | 58.93 | 7.61 | 22.80 |

WORKING EXAMPLE 27

6-Allyl-8-pentyl-2,3-dihydro-1H-imidazo[2',1':5,1-]pyrazolo[3,4-d]pyrimidine-7,9(6H,8H)-dione To a stirred solution of 7-allyl-3-amino-2-(2-chloroethyl)-5-pentyl-2H-pyrazolo[3,4-d]pyrimidine-4,6(5H,7H)-dione(4.1 g) in DMF(80 ml) was added in portions sodium hydride (60% oil, 0.6 g) under ice-cooling. The mixture was stirred at room temperature for further 5 hours. The reaction mixture was concentrated to dryness and the residue added to ice-water. This was followed by stirring for a while, whereupon crystals precipitated out. The crystals were collected by filtration and recrystallized from ethyl acetate/hexane to give colorless crystals(2.42 g, 66%), m.p. 145°–146° C.

Elemental Analysis for $C_{15}H_{21}N_5O_2$

|  | C(%) | H(%) | N(%) |
| --- | --- | --- | --- |
| Calcd. | 59.39 | 6.98 | 23.09 |
| Found | 59.44 | 7.00 | 23.18 |

WORKING EXAMPLE 28

6-Isobutyl-8-pentyl-2,3-dihydro-1H-imidazo[2',1':5,1-]pyrazolo[3,4-d]pyrimidine-7,9(6H,8H)-dione To a stirred solution of 3amino-2-(2-chloroethyl)-7-isobutyl-5-pentyl-2H-pyrazolo[3,4-d]pyrimidine-4,6(5H,7H)-dione(3.6 g) in DMF(80 ml) was added in portions sodium hydride (60% oil, 0.55 g) under ice-cooling. The mixture was stirred at room temperature for further 5 hours. The reaction mixture was concentrated to dryness and the residue added to ice-water. This was followed by stirring for a while, whereupon crystals precipitated out. The crystals were collected by filtration, followed by recrystallization from ethyl acetate/hexane to give colorless crystals(2.36 g, 73%), m.p. 171°–172° C.

Elemental Analysis for $C_{16}H_{25}N_5O_2$

|  | C(%) | H(%) | N(%) |
| --- | --- | --- | --- |
| Calcd. | 60.17 | 7.89 | 21.93 |
| Found | 60.18 | 7.95 | 22.00 |

WORKING EXAMPLE 29

6,8-Diallyl-2,3-dihydro-1H-imidazo[2',1':5,1-]pyrazolo[3,4-d]pyrimidine-7,9(6H,8H)-dione To a stirred solution of 5,7-diallyl-3-amino-2-(2-chloroethyl)-2H-pyrazolo[3,4-d]pyrimidine-4,6(5H,7H)-dione(6.17 g) in DMF(80 ml) was added in portions sodium hydride (60% oil, 1.2 g) under ice-cooling. The mixture was stirred at room temperature for further 5 hours. The reaction mixture was concentrated to dryness. The concentrate was added to ice-water and the residue was stirred for a while, whereupon crystals precipitated out. The crystals were collected by filtration and recrystallized from methylene chloride/hexane to give colorless crystals(3.6 g, 66%), m.p. 181°–183° C.

Elemental Analysis for $C_{13}H_{15}N_5O_2$

|  | C(%) | H(%) | N(%) |
| --- | --- | --- | --- |
| Calcd. | 57.13 | 5.53 | 25.63 |
| Found | 56.72 | 5.56 | 25.18 |

WORKING EXAMPLE 30

6,8-Diisobutyl-1-methyl-2,3-dihydro-1H-imidazo[2;,1':5,1]pyrazolo[3,4-d]pyrimidine-7,9(6H,8H)-dione To a stirred solution of 2-(2-chloroethyl)-5,7-diisobutyl-3-methylamino-2H-pyrazolo[3,4-d]pyrimidine-4,6(5H,7H)-dione (0.7 g) in DMF(10 ml) was added in portions sodium hydride(60% oil, 0.2 g) under ice-cooling. The mixture was stirred at room temperature for further two hours. The reaction mixture was concentrated to dryness. The concentrate was added to ice-water and the residue was stirred for a while, whereupon crystals precipitated out, which were collected by filtration, followed by recrystallization from isopropyl ether to give colorless crystals(0.4 g, 64%), m.p. 109°–111° C.

Elemental Analysis for $C_{16}H_{25}N_5O_2$

|  | C(%) | H(%) | N(%) |
| --- | --- | --- | --- |
| Calcd. | 60.17 | 7.89 | 21.93 |
| Found | 60.14 | 7.90 | 21.95 |

WORKING EXAMPLE 31

6-Butyl-1-butyryl-8-propyl-2,3-dihydro-1H-imidazo[2',1':5,1]pyrazolo[3,4-d]pyrimidine-7,9(6H,8H)-dione A solution of 6-butyl-8-propyl-2,3-dihydro-1H-imidazo[2',1':5,1]pyrazolo[3,4-d]pyrimidine-7,9(6H,8H)-dione(1.2 g) and butyric anhydride(1.3 ml) in pyridine(15 ml) was stirred at 50°–60° C. for 15 hours. The reaction mixture was concentrated to dryness to give a syrup, which was purified by flash chromatography(silica gel, chloroform) to obtain a pale yellow syrup, which was crystallized from hexane/isopropyl ether to give colorless crystals(0.6 g, 40%), m.p. 60°–63° C.

Elemental Analysis for $C_{18}H_{27}N_5O_3$

|  | C(%) | H(%) | N(%) |
| --- | --- | --- | --- |
| Calcd. | 59.82 | 7.53 | 19.38 |
| Found | 59.57 | 7.54 | 19.35 |

WORKING EXAMPLE 32

6-Isobutyl-1-propionyl-8-propyl-2,3-dihydro-1H-imidazo[2',1':5,1]pyrazolo[3,4-pyrimidine-7,9(6H,8H)-dione A solution of 6-isobutyl-8-propyl-2,3-dihydro-1H-imidazo [2',1':5,1]pyrazolo[3,4-d]pyrimidine-7,9(6H,8H)-dione(1.2 g) and propionic anhydride(1.2 ml)in pyridine(20 ml) was stirred at 100° C. for 44 hours. The reaction mixture was concentrated to dryness to give a syrup, which was purified by flash chromatography. The resultant syrupy product was crystallized from methylene chloride/hexane to obtain colorless crystals(1.17 g, 98%), m.p. 118°–120° C.

Elemental Analysis for $C_{17}H_{25}N_5O_3$

|  | C(%) | H(%) | N(%) |
| --- | --- | --- | --- |
| Calcd. | 58.77 | 7.25 | 20.16 |
| Found | 58.66 | 7.19 | 19.77 |

WORKING EXAMPLE 33

1-Propionyl-6,8-dipropyl-2,3-dihydro-1H-imidazo[2',1':5,1]pyrazolo[3,4-d]pyrimidine-7,9(6H,8H)-dione A solution of 6,8-dipropyl-2,3-dihydro-1H-imidazo[2',1': 5,1]pyrazolo[3,4-d]pyrimidine-7,9(6H,8H)-dione(1.5 g) and propionic anhydride(1.5 ml) in pyridine(20 ml) was stirred at 100° C. for 24 hours. The reaction mixture was concentrated to dryness to give a syrup, which was purified by flash chromatography. The resultant syrupy product was crystallized from hexane to obtain colorless crystals (1.2 g, 67%), m.p. 82°–84° C.

| | Elemental Analysis for $C_{16}H_{23}N_5O_3$: | | |
|---|---|---|---|
| | C (%) | H (%) | N (%) |
| Calcd.: | 57.64; | 6.95; | 21.01 |
| Found: | 57.68; | 6.89; | 20.67 |

WORKING EXAMPLE 34

1-Butyryl-6,8-dipropyl-2,3-dihydro-1H-imidazo[2',1':5,1]pyrazolo[3,4-d]pyrimidine-7,9(6H,8H)-dione A solution of 6,8-dipropyl-2,3-dihydro-1H-imidazo[2',1': 5,1]pyrazolo[3,4-d]pyrimidine-7,9(6H,8H)-dione(1.5 g) and butyric anhydride(1.6 ml) in pyridine(20 ml) was stirred at 100° C. for 24 hours. The reaction mixture was concentrated to dryness to give a syrup, which was purified by flash chromatography. The resultant syrupy product was crystallized from hexane to obtain colorless crystals (0.82 g, 44%), m.p. 72°–74° C.

| | Elemental Analysis for $C_{17}H_{25}N_5O_3$: | | |
|---|---|---|---|
| | C (%) | H (%) | N (%) |
| Calcd.: | 58.77; | 7.25; | 20.16 |
| Found: | 58.99; | 7.21; | 19.84 |

WORKING EXAMPLE 35

6,8-Diallyl-1-propionyl-2,3-dihydro-1H-imidazo[2',1':5,1]pyrazolo[3,4-d]pyrimidine-7,9(6H,8H)-dione A solution of 6,8-diallyl-2,3-dihydro-1H-imidazo[2',1': 5,1]pyrazolo[3,4-d]pyrimidine-7,9(6H,8H)-dione(1.0 g) and propionic anhydride(1.0 ml) in pyridine(15 ml) was stirred at 100° C. for 43 hours. The reaction mixture was concentrated to dryness to give a syrup, which was purified by flash chromatography. The resultant syrupy product was crystallized from methylene chloride/isopropyl ether to obtain colorless crystals(0.89 g, 74%), m.p. 116°–118° C.

| | Elemental Analysis for $CH_{16}H_{19}N_5O_3$: | | |
|---|---|---|---|
| | C (%) | H (%) | N (%) |
| Calcd.: | 58.35; | 5.81; | 21.26 |
| Found: | 57.97; | 5.82; | 20.97 |

WORKING EXAMPLE 36

6-Pentyl-1-propionyl-8-propyl-2,3-dihydro-1H-imidazo[2',1': 5,1]pyrazolo[3,4-d]pyrimidine-7,9(6H,8H)-dione A solution of 6-pentyl-8-propyl-2,3-dihydro-1H-imidazo[2',1':5,1]pyrazolo[3,4-d]pyrimidine-7,9(6H,8H)-dione(1.5 g) and propionic anhydride(1.5 ml) in pyridine(30 ml) was stirred at 100° C. for 24 hours. The reaction mixture was concentrated to dryness to give a syrup, which was purified by flash chromatography. The resultant syrupy product was crystallized from isopropyl ether/hexane to obtain colorless crystals(1.16 g, 65%), m.p. 99°–100° C.

| | Elemental Analysis for $C_{18}H_{27}N_5O_3$: | | |
|---|---|---|---|
| | C (%) | H (%) | N (%) |
| Calcd.: | 59.82; | 7.53; | 19.38 |
| Found: | 59.52; | 7.52; | 19.29 |

WORKING EXAMPLE 37

6-Allyl-1-propionyl-8-propyl-2,3-dihydro-1H-imidazo[2',1': 5,1]pyrazolo[3,4-d]pyrimidine-7,9(6H,8H)-dione A solution of 6-allyl-8-propyl-2,3-dihydro-1H-imidazo[2',1': 5,1]pyrazolo[3,4-d]pyrimidine-7,9(6H,8H)-dione(0.8 g) and propionic anhydride(1.0 ml) in pyridine(15 ml) was stirred at 100° C. for 44 hours. The reaction mixture was concentrated to dryness to give a syrup, which was purified by flash chromatography. The resultant syrupy product was crystallized from isopropyl ether/hexane to obtain colorless crystals(0.8 g, 83%), m.p. 83°–85° C.

| | Elemental Analysis for $C_{16}H_{21}N_5O_3$: | | |
|---|---|---|---|
| | C (%) | H (%) | N (%) |
| Calcd.: | 57.99; | 6.39; | 21.13 |
| Found: | 57.82; | 6.39; | 21.14 |

WORKING EXAMPLE 38

6,8-Dibutyl-1-butyryl-2,3-dihydro-1H-imidazo[2',1':5,1-]pyrazolo[3,4-d]pyrimidine-7,9(6H,8H)-dione A solution of 6,8-dibutyl-2,3-dihydro-1H-imidazo[2',1': 5,1]pyrazolo[3,4-d]pyrimidine-7,9(6H,8H)-dione(0.94 g) and butyric anhydride(0.5 ml) in pyridine(10 ml) was stirred at 50°–60° C. for 15 hours.

The reaction mixture was concentrated to dryness to give a syrup, which was purified by flash chromatography(silica gel, chloroform) to obtain a pale yellow syrup. The product was crystallized from hexane/isopropyl ether to obtain colorless crystals(0.45 g, 39%), m.p. 83°–86° C.

| | Elemental Analysis for $C_{19}H_{29}N_5O_3$: | | |
|---|---|---|---|
| | C (%) | H (%) | N (%) |
| Calcd.: | 60.78; | 7.78; | 18.65 |
| Found: | 60.44; | 7.89; | 18.51 |

WORKING EXAMPLE 39

1-Acetyl-6,8-dibutyl-2,3-dihydro-1H-imidazo[2',1':5,1-]pyrazolo[3,4-d]pyrimidine-7,9(6H,8H)-dione A solution of 6,8-dibutyl-2,3-dihydro-1H-imidazo[2',1': 5,1]pyrazolo[3,4-d]pyrimidine-7,9(6H,8H)-dione(1.5 g) and acetic anhydride(1.4 ml) in pyridine(20 ml) was stirred at 50°-60° C. for 15 hours. The reaction mixture was concentrated to dryness and purified by flash chromatography(silica gel, chloroform) to obtain a pale yellow syrup. The product was crystallized from aqueous methanol to obtain colorless crystals(1.2 g, 70%), m.p. 120°-122° C..

| Elemental Analysis for $C_{17}H_{25}N_5O_3$: | | | |
|---|---|---|---|
| | C (%) | H (%) | N (%) |
| Calcd.: | 56.19; | 6.93; | 19.27 |
| Found: | 55.94; | 6.92; | 19.37 |

WORKING EXAMPLE 40

1-Acetyl-6-butyl-8-propyl-2,3-dihydro-1H-imidazo[2',1': 5,1]pyrazolo[3,4-d]pyrimidine-7,9(6H,8H)-dione A solution of 6-butyl-8-propyl-2,3-dihydro-1H-imidazo[2',1': 5,1]pyrazolo[3,4-d]pyrimidine-7,9(6H,8H)-dione(1.0 g) and acetic anhydride(1.0 ml) in pyridine(15 ml) was stirred at 50°-60° C. for 15 hours. The reaction mixture was concentrated to dryness to give a syrup, which was purified by flash chromatography (silica gel, chloroform), to obtain a pale yellow syrup. The syrup was crystallized from hexane/isopropyl ether to afford colorless crystals (0.79 g, 69%), m.p. 98°-100° C.

| Elemental Analysis for $C_{18}H_{23}N_5O_3$: | | | |
|---|---|---|---|
| | C (%) | H (%) | N (%) |
| Calcd.: | 57.64; | 6.95; | 21.01 |
| Found: | 57.55; | 6.96; | 20.96 |

WORKING EXAMPLE 41

6,8-Dibutyl-1-propionyl-2,3-dihydro-1H-imidazo[2',1': 5,1]pyrazolo[3,4-d]pyrimidine-7,9(6H,8H)-dione A solution of 6,8-dibutyl-2,3-dihydro-1H-imidazo[2',1': 5,1]pyrazolo[3,4-d]pyrimidine-7,9(6H,8H)-dione(1.5 g) and propionic anhydride(0.9 ml) in pyridine(20 ml) was stirred at 50°-60° C. for 20 hours. The reaction mixture was concentrated to dryness to give a syrupy product, which was purified by flash chromatography (silica gel, chloroform) to obtain a pale yellow syrup. The syrup was crystallized from hexane/isopropyl ether to afford colorless crystals(0.75 g, 43%), m.p. 93°-95° C.

| Elemental Analysis for $C_{18}H_{23}N_5O_3$: | | | |
|---|---|---|---|
| | C (%) | H (%) | N (%) |
| Calcd.: | 59.82; | 7.53; | 19.38 |
| Found: | 59.72; | 7.61; | 19.36 |

WORKING EXAMPLE 42

6,8-Dibutyl-1-methoxycarbonyl-2,3-dihydro-1H-imidazo[2',1': 5,1]pyrazolo[3,4-d]pyrimidine-7,9(6H,8H)-dione To a suspension of 6,8-dibutyl-2,3-dihydro-1H-imidazo[2',1':5,1]pyrazolo[3,4-d]pyrimidine-7,9(6H,8H)-dione (1.5 g) and triethylamine(2.0 ml) in dioxane(50 ml)was added methyl chloroformate(0.75 ml) dropwise, while stirring under ice-cooling, and the mixture was stirred at room temperature for 5 hours, followed by stirring at 50°-60° C. for further 20 hours. The reaction mixture was concentrated to dryness, and the concentrate was extracted with chloroform. The chloroform layer was washed with water, dried and concentrated to give a syrupy product, which was purified by flash chromatography (silica gel, chloroform) to obtain colorless crystals(0.8 g, 45%), m.p. 138°-140° C.

| Elemental Analysis for $C_{17}H_{25}N_5O_4$: | | | |
|---|---|---|---|
| | C (%) | H (%) | N (%) |
| Calcd.: | 56.19; | 6.93; | 19.27 |
| Found: | 55.94; | 6.92; | 19.37 |

WORKING EXAMPLE 43

6-Butyl-8-propyl-1H-imidazo[2',1':5,1]pyrazolo[3,4-d]pyrimidine-7,9(6H,8H)-dione To a solution of 6-butyl-8-propyl-2,3-dihydro-1H-imidazo[2',1':5,1]pyrazolo[3,4-d]pyrimidine-7,9(6H,8H)-dione(0.6 g) in DMF(12 ml) was added potassium carbonate(0.32 g), and the mixture was stirred at 100° C. for 34 hours. The reaction mixture was concentrated to dryness. To the concentrate was added methylene chloride, and insolubles were filtered off. The filtrate was concentrated to give a syrupy product, which was purified by flash chromatography(silica gel, chloroform) to give crystals, followed by recrystallization from methylene chloride/hexane to obtain pale yellow prisms(0.29 g, 49%), m.p. 235°-236° C.

| Elemental Analysis for $C_{14}H_{19}N_5O_2$: | | | |
|---|---|---|---|
| | C (%) | H (%) | N (%) |
| Calcd.: | 58.12; | 6.62; | 24.20 |
| Found: | 58.17; | 6.61; | 24.28 |

WORKING EXAMPLE 44

6,8-Dipropyl-1H-imidazo[2',1':5,1]pyrazolo[3,4-d]pyrimidine-7,9(6H,8H)-dione

A solution of 6,8-dipropyl-2,3-dihydro-1H-imidazo[2',1': 5,1]pyrazolo[3,4-d]pyrimidine-4,6(5H,7H)-dione(1.6 g) and benzoyl peroxide(2.1 g) in chloroform(50 ml) was heated under reflux for 15 hours. The reaction mixture was concentrated to dryness, and the concentrate was dissolved in chloroform, followed by washing with an aqueous solution of sodium carbonate. The resulting solution was dried and concentrated to dryness. The concentrate was purified by flash chromatography. The crystals were recrystallized from methylene/hexane to obtain colorless crystals (1.1 g, 71%), m.p. 243°-245° C.

| Elemental Analysis for $C_{13}H_{17}N_5O_2$: | | | |
|---|---|---|---|
| | C (%) | H (%) | N (%) |
| Calcd.: | 56.72; | 6.22; | 25.44 |
| Found: | 56.33; | 6.24; | 25.38 |

WORKING EXAMPLE 45

6,8-Diallyl-1H-imidazo[2',1':5,1]pyrazolo[3,4-d]pyrimidine-7,9(6H,8H)-dione

A solution of 6,8-diallyl-2,3-dihydro-1H-imidazo[2',1': 5,1]pyrazolo[3,4-d]pyrimidine-4,6(5H,7H)-dione(2.1 g) and benzoyl peroxide(2.8 g) in chloroform(60 ml) was heated under reflux for 15 hours. The reaction mixture was concentrated to dryness, and the concentrate was dissolved in chloroform, followed by washing with an aqueous solution of sodium carbonate. The resulting solution was dried and concentrated to dryness. The concentrate was purified by flash chromatography to give a crystalline product, which was recrystallized from aqueous ethanol to afford colorless crystals(1.3 g, 62%), m.p. 235°–239° C.

| Elemental Analysis for $C_{13}H_{13}N_5O_2$: | | | |
|---|---|---|---|
| | C (%) | H (%) | N (%) |
| Calcd.: | 57.56; | 4.83; | 25.82 |
| Found: | 57.47; | 4.90; | 25.69 |

WORKING EXAMPLE 46

6,8-Dibutyl-1H-imidazo[2',1':5,1]pyrazolo[3,4-d]pyrimidine7,9(6H,8H)-dione

A solution of 6,8-dibutyl-2,3-dihydro-1H-imidazo[2',1': 5,1]pyrazolo[3,4-d]pyrimidine-4,6(5H,7H)-dione(1.9 g) and benzoyl peroxide(2.26 g) in chloroform(50 ml) was heated under reflux for 10 hours. The reaction mixture was concentrated to dryness, and the concentrate was dissolved in chloroform, followed washing with an aqueous solution of sodium carbonate. The resulting solution was dried and concentrated to dryness, and the concentrate was purified by flash chromatography. Crystals obtained were recrystallized from chloroform/isopropyl ether to obtain colorless crystals(1.2 g, 64%), m.p. 200°–202° C.

| Elemental Analysis for $C_{15}H_{21}N_5O_2$: | | | |
|---|---|---|---|
| | C (%) | H (%) | N (%) |
| Calcd.: | 59.39; | 6.98; | 23.09 |
| Found: | 59.37; | 6.98; | 23.17 |

WORKING EXAMPLE 47

6,8-Dibutyl-1-methyl-1H-imidazo[2',1':5,1-]pyrazolo[3,4-d]pyrimidine-7,9(6H,8H)-dione A solution of 6,8-dibutyl-1-methyl-2,3-dihydro-1H-imidazo [2',1':5,1]pyrazolo[3,4-d]pyrimidine-4,6(5H,7H)-dione(1.5 g) and benzoyl peroxide(1.7 g) in chloroform(50 ml) was heated under reflux for 5 hours. The reaction mixture was concentrated to dryness, and the concentrate was dissolved in chloroform. The solution was washed with an aqueous solution of sodium carbonate, followed by drying and concentration to dryness. The concentrate was purified by flash chromatography to give crystals, which were recrystallized from isopropyl ether to afford colorless crystals (1.1 g, 74%), m.p. 153°–155° C.

| Elemental Analysis for $C_{16}H_{23}N_5O_2$: | | | |
|---|---|---|---|
| | C (%) | H (%) | N (%) |
| Calcd.: | 60.55; | 7.30; | 22.07 |
| Found: | 60.58; | 7.33; | 22.19 |

WORKING EXAMPLE 48

6-Isobutyl-8-propyl-1H-imidazo[2',1':5,1]pyrazolo[3,4-d]pyrimidine-7,9(6H,8H)-dione A solution of 6-isobutyl-8-propyl-2,3-dihydro-1H-imidazo[2',1':5,1]pyrazolo[3,4-d]pyrimidine-4,6(5H,7H)-dione(1.3 g) and benzoyl peroxide(1.6 g) in chloroform(40 ml) was heated under reflux for 15 hours. The reaction mixture was concentrated to dryness, and the concentrate was dissolved in chloroform. The solution was washed with an aqueous solution of sodium carbonate. The resulting solution was dried and concentrated to dryness. The concentrate was purified by flash chromatography to give a crystalline product, which was recrystallized from aqueous ethanol to afford colorless crystals(0.8 g, 63%), m.p. 283°–287° C.

| Elemental Analysis for $C_{14}H_{19}N_5O_2$: | | | |
|---|---|---|---|
| | C (%) | H (%) | N (%) |
| Calcd.: | 58.12; | 6.62; | 24.20 |
| Found: | 58.01; | 6.67; | 23.99 |

WORKING EXAMPLE 49

6-Allyl-8-propyl-1H-imidazo[2',1':5,1]pyrazolo[3,4-d]pyrimidine-7,9(6H,8H)-dione A solution of 6-allyl-8-propyl-2,3-dihydro-1H-imidazo[ 2',1':5,1]pyrazolo[3,4-d]pyrimidine-4,6(5H,7H)-dione(1.5 g) and benzoyl peroxide(2.0 g) in chloroform(50 ml) was heated under reflux for 15 hours. The reaction mixture was concentrated to dryness, and the concentrate was dissolved in chloroform. This was followed by washing with an aqueous solution of sodium carbonate. The resulting solution was dried and concentrated to dryness. The concentrate was purified by flash chromatography to give a crystalline product, which was recrystallized from aqueous ethanol to afford colorless crystals(1.0 g, 70%), m.p. 240°–242° C.

| Elemental Analysis for $C_{13}H_{15}N_5O_2$: | | | |
|---|---|---|---|
| | C (%) | H (%) | N (%) |
| Calcd.: | 57.13; | 5.53; | 25.63 |
| Found: | 56.98; | 5.57; | 25.52 |

WORKING EXAMPLE 50

6-Pentyl-8-propyl-1H-imidazo[2',1':5,1]pyrazolo[3,4-d]pyrimidine-7,9(6H,8H)-dione A solution of 6-pentyl-8-propyl-2,3-dihydro-1H-imidazo[2',1':5,1]pyrazolo[3,4-d]pyrimidine-4,6(5H,7H)-dione(1.8 g) and benzoyl peroxide(2.1 g) in chloroform(60 ml) was heated under reflux for 15 hours. The reaction mixture was concentrated to dryness, and the concentrate was dissolved in chloroform.

This was followed by washing with an aqueous solution of sodium carbonate. The resulting solution was dried and concentrated to dryness. The concentrate was purified by flash chromatography to give a crystalline product, which was recrystallized from aqueous ethanol to afford colorless crystals(1.1 g, 62%), m.p. 223°–224° C.

Elemental Analysis for $C_{15}H_{21}N_5O_2$:

|  | C (%) | H (%) | N (%) |
| --- | --- | --- | --- |
| Calcd.: | 59.39; | 6.98; | 23.09 |
| Found: | 59.35; | 7.01; | 22.89 |

WORKING EXAMPLE 51

2,3-Dimethyl-6,8-dipropyl-1H-imidazo[2',1':5,1-]pyrazolo[3,4-d]pyrimidine-7,9(6H,8H)-dione A mixture of 3-amino-5,7-dipropylpyrazolo[3,4-d]pyrimidine-4,6(5H,7H)-dione(1.0 g), 3-chloro-2-butanone(1.2 g), potassium iodide(0.7 g) and potassium carbonate(1.1 g) in acetonitrile(40 ml) was stirred at room temperature for three days. The reaction mixture was concentrated to dryness and there was added water, whereupon crystals precipitated out. The crystals were washed with water and dried to obtain crystals(1.2 g). A mixture of the crystals and a catalytic amount of p-toluenesulfonic acid in toluene(30 ml) was heated under reflux for 14 hours. The reaction mixture was cooled to give a crystalline product. The crystals were collected by filtration and washed with a small volume of toluene to obtain colorless crystals(0.98 g, 86%), m.p. 294°–295° C.

Elemental Analysis for $C_{15}H_{21}N_5O_2$

|  | C (%) | H (%) | N (%) |
| --- | --- | --- | --- |
| Calcd. | 59.39 | 6.98 | 23.09 |
| Found | 59.36 | 7.00 | 22.98 |

WORKING EXAMPLE 52

2-Phenyl-6,8-dipropyl-1H-imidazo[2',1':5,1]pyrazolo[3,4-d]-pyrimidine-7,9(6H,8H)-dione A mixture of 3-amino-5,7-dipropylpyrazolo[3,4-d]pyrimidine-4,6(5H,7H)-dione(2 g), phenacyl chloride(1.5 g), potassium iodide(1.6 g) and potassium carbonate(1.1 g) in acetonitrile(80 ml) was stirred at room temperature for three days. The reaction mixture was concentrated to dryness. There was added water, whereupon crystals precipitated out. The crystals were washed with water and dried to obtain crystals(2.4 g). A mixture of the crystals and a catalytic amount of p-toluenesulfonic acid in toluene (50 ml) was heated under reflux for 5 hours. The reaction mixture was cooled and left standing to yield crystals, which were recrystallized from DMF/ethyl acetate to afford colorless crystals(1.98 g, 87%), m.p. 262°–263° C.

Elemental Analysis for $C_{19}H_{21}N_5O_2$

|  | C (%) | H (%) | N (%) |
| --- | --- | --- | --- |
| Calcd. | 64.94 | 6.02 | 19.93 |
| Found | 64.65 | 6.07 | 20.06 |

WORKING EXAMPLE 53

6-Butyl-2-phenyl-8-propyl-1H-imidazo[2',1':5,1-]pyrazolo[3,4-d]pyrimidine-7,9(6H,8H)-dione A mixture of 3-amino-7-butyl-5-propylpyrazolo[3,4-d]pyrimidine-4,6(5H,7H)-dione(1.4 g), phenacyl chloride(1.2 g) and triethylamine(0.7 g) was stirred in methyl ethyl ketone (40 ml) at 60° C. for 4 days. The reaction mixture was filtered and the filtrate was concentrated to dryness. The concentrate was purified by silica gel chromatography to obtain colorless crystals(0.94 g). The crystalline product was subjected to heating under reflux in toluene(30 ml) together with a catalytic amount of p-toluenesulfonic acid for 14 hours. The reaction mixture was concentrated to dryness, and the concentrate was recrystallized from aqueous alcohol to obtain colorless needles (0.79 g, 41%), m.p. 263°–265° C.

Elemental Analysis for $C_{20}H_{23}N_5O_2 \cdot 1/2H_2O$

|  | C (%) | H (%) | N (%) |
| --- | --- | --- | --- |
| Calcd. | 64.15 | 6.45 | 18.70 |
| Found | 64.05 | 6.37 | 18.75 |

WORKING EXAMPLE 54

6,8-Dibutyl-2-phenyl-1H-imidazo[2',1':5,1-]pyrazolo[3,4-d]pyrimidine-7,9(6H,8H)-dione A mixture of 3amino-5,7-dibutylpyrazolo[3,4-d]pyrimidine-4,6(5H,7H)-dione(2 g), phenacyl bromide(2.17 g) and triethylamine(1.1 g) in methyl ethyl ketone(60 ml) was stirred at 50° C. for 95 hours. The reaction mixture was subjected to filtration, and the filtrate was concentrated to dryness. The concentrate was dissolved in toluene(50 ml), to which was added a catalytic amount of p-toluenesulfonic acid, and the mixture was heated under reflux for 14 hours. The reaction mixture was concentrated to dryness, and the concentrate was purified by flash chromatography. A crude crystalline product thus obtained was recrystallized from aqueous alcohol to afford colorless crystals(0.74 g, 27%), m.p. 246°–248° C.

Elemental Analysis for $C_{21}H_{25}N_5O_2 \cdot 1/2H_2O$

|  | C (%) | H (%) | N (%) |
| --- | --- | --- | --- |
| Calcd. | 64.93 | 6.75 | 18.03 |
| Found | 64.97 | 6.76 | 17.92 |

WORKING EXAMPLE 55

6,8-Dibutyl-2-methyl-1H-imidazo[2',1':5,1-]pyrazolo[3,4-d]pyrimidine-7,9(6H,8H)-dione A mixture of 3-amino-5,7-dibutylpyrazolo[3,4-d]pyrimidine-4,6(5H,7H)-dione(1 g), bromoacetone(0.6 g) and triethylamine (0.4 g) in methyl ethyl ketone(30 ml) was stirred at 50° C. for 68 hours. The reaction mixture was filtered, and the filtrate was concentrated to dryness. The concentrate was purified by silica gel chromatography to obtain colorless crystals (0.88 g), which were heated in toluene(30 ml) containing a catalytic amount of p-toluenesulfonic acid under reflux for 14 hours. The reaction mixture was concentrated to dryness, and the concentrate was recrystallized from aqueous alcohol to afford colorless needles(0.61 g, 55%), m.p. 268°–270° C.

| Elemental Analysis for $C_{16}H_{23}N_5O_2$ | | | |
|---|---|---|---|
| | C (%) | H (%) | N (%) |
| Calcd. | 60.55 | 7.30 | 22.07 |
| Found | 60.60 | 7.31 | 22.00 |

WORKING EXAMPLE 56

2,3-Dibromo-6,8-dibutyl-1H-imidazo[2',1':5,1-]pyrazolo[3,4-d]pyrimidine-7,9(6H,8H)-dione To a solution of 6,8-dibutyl-1H-imidazo[2',1':5,1-]pyrazolo[3,4-d]pyrimidine-7,9(6H,8H)-dione(1.0 g) in acetic acid(10 ml) was added dropwise a solution of acetic acid (3 ml) containing bromine(0.34 ml) at room temperature. The mixture was stirred for a while at room temperature, whereupon crystals precipitated out. This was followed by washing with a small quantity of alcohol to afford colorless crystals, m.p. 245°–250° C.(decomp.).

| Elemental Analysis for $C_{15}H_{14}Br_2N_5O_2$ | | | |
|---|---|---|---|
| | C (%) | H (%) | N (%) |
| Calcd. | 39.07 | 4.15 | 15.19 |
| Found | 39.16 | 4.07 | 15.62 |

WORKING EXAMPLE 57

6-Butyl-8-propyl-1H-imidazo[2',1':5,1]pyrazolo[3,4-d]pyrimidine-3,7,9(2H,6H,8H)-trione To a solution of 7-butyl-3-carboxymethylamino-5-propylpyrazolo[3,4-d]pyrimidine-4,6(5H,7H)-dione(1.0 g) in methylene chloride(25 ml) was added thionyl chloride(4 ml). The mixture was heated under reflux for 1.5 hour. The reaction mixture was concentrated to dryness to give crude crystals, which were recrystallized from methylene chloride/isopropyl ether to afford colorless crystals(0.8 g, 85%), m.p. 258°–259° C.

| Elemental Analysis for $C_{14}H_{19}N_5O_3$ | | | |
|---|---|---|---|
| | C (%) | H (%) | N (%) |
| Calcd. | 55.07 | 6.27 | 22.94 |
| Found | 54.97 | 6.12 | 23.00 |

WORKING EXAMPLE 58

6-Butyl-8propyl-1H-imidazo[2',1':5,1]pyrazolo[3,4-d]pyrimidine-2,7,9(3H,6H,8H)-trione A solution of 3-amino-7-butyl-2-ethoxycarbonylmethyl-5-propyl-2H-pyrazolo-[3,4-d]pyrimidine-4,6(5H,7H)-dione(1.85 g) in ethanol(35 ml) containing sodium(0.31 g) was stirred at room temperature for 30 minutes. The reaction mixture was concentrated to dryness. The concentrate was dissolved in ice-water, which was made weakly acid with 1N-HCl. Precipitating crystals were collected by filtration, and recrystallized from methylene chloride/ethanol to afford colorless needles(0.84 g, 52%), m.p. 266°–269° C.

| Elemental Analysis for $C_{14}H_{19}N_5O_3$ | | | |
|---|---|---|---|
| | C (%) | H (%) | N (%) |
| Calcd. | 55.07 | 6.27 | 22.94 |
| Found | 54.99 | 6.23 | 22.82 |

WORKING EXAMPLE 59

1-Butyl-3-propyl-5,6,7,8-tetrahydropyrimido[2',1':5,1-]pyrazolo[3,4-d]pyrimidine-2,4(1H,3H)-dione To a stirred solution of 3-amino-7-butyl-2-(3-chloropropyl)-5-propyl-2H-pyrazolo[3,4-d]pyrimidine-4,6(5H,7H)-dione(2.1 g) in DMF(30 ml) was added sodium hydride(60% oil, 0.7 g) in portions under ice-cooling. The mixture was stirred at room temperature for further 5 hours. The reaction mixture was concentrated to dryness and the concentrate was added to ice-water. The mixture was stirred for a while, whereupon crystals precipitated out. The crystals were collected by filtration and recrystallized from aqueous alcohol to afford colorless crystals(0.6 g, 32%), m.p. 147°–150° C.

| Elemental Analysis for $C_{15}H_{23}N_5O_2$ | | | |
|---|---|---|---|
| | C (%) | H (%) | N (%) |
| Calcd. | 59.00 | 7.59 | 22.93 |
| Found | 59.19 | 7.58 | 22.83 |

WORKING EXAMPLE 60

1-Butyl-5-methyl-3-propyl-5,6,7,8-tetrahydropyrimido[2',1': 5,1]pyrazolo[3,4-d]pyrimidine-2,4(1H,3H)-dione To a stirred solution of 7-butyl-2-(3-chloropropyl)-3-methylamino-5-propyl-2H-pyrazolo[3,4-d]pyrimidine-4,6(5H,7H)-dione(2.0 g) in DMF(30 ml) was added sodium hydride(60% oil, 0.67 g), in portions under ice-cooling. The mixture was stirred at room temperature for further 5 hours. The reaction mixture was concentrated to dryness and the concentrate was added to ice-water. The mixture was stirred for a while, whereupon crystals precipitated out. The crystals were collected by filtration and recrystallized from isopropyl ether to afford colorless crystals(1.55 g, 90%), m.p. 94°–98° C.

| Elemental Analysis for $C_{16}H_{25}N_5O_2$ | | | |
|---|---|---|---|
| | C (%) | H (%) | N (%) |
| Calcd. | 60.17 | 7.89 | 21.93 |
| Found | 60.19 | 7.89 | 21.95 |

WORKING EXAMPLE 61

1-Butyl-5-methyl-3-propyl-6,7,8,9-tetrahydro-5H-pyrimido[5',4':4,3]pyrazolo[1,5-a][1,3]diazepine-2,4(1H,3H)-dione To a stirred solution of 7-butyl-2-(4-chlorobutyl)-3-methylamino-5-propyl-2H-pyrazolo[3,4-d]pyrimidine-4,6(5H,7H)-dione(2.0 g) in DMF(30 ml) was added sodium hydride(60% oil, 0.65 g) in portions under ice-cooling. The mixture was stirred at room temperature for further 5 hours. The reaction mixture was concentrated to dryness and was added to ice-water, followed by neutralizing with 1N-HCl and extraction with chloroform. The chloroform layer was washed with water, dried and concentrated to dryness to give a syrupy product. The product was purified by flash chromatography(silica gel, chloroform) to give crystals, which recrystallized from isopropyl ether/hexane to afford colorless crystals(1.2 g, 67%), m.p. 63°–65° C.

| Elemental Analysis for $C_{17}H_{27}N_5O_2$ | | | |
|---|---|---|---|
| | C (%) | H (%) | N (%) |
| Calcd. | 61.24 | 8.16 | 21.00 |
| Found | 61.38 | 8.12 | 21.00 |

WORKING EXAMPLE 62

6,8-Diisobutyl-2,3-dihydro-1H-imidazo[2',1':5,1-]pyrazolo[3,4-d]pyrimidine-7,9(6H,8H)-dione To a stirred solution of 2-(2-Chloroethyl)-6,8-diisobutyl-2H-pyrazolo[3,4-d]pyrimidine (3.6 g) in DMF(50 ml) was added sodium hydride (60% oil, 0.64 g) in portions by cooling with ice-bath. The mixture was stirred at room temperature for 3 hr and concentrated to dryness.

The resulting residue was poured into ice-water yield a crystalline product. After filtration, the crystals were recrystallized from methylene chloride/isopropylether to give colorless crystals (2.15 g, 67%), m.p. 244°–245° C.

| Elemental Analysis for $C_{15}H_{23}N_5O_2$ | | | |
|---|---|---|---|
| | C (%) | H (%) | N (%) |
| Calcd. | 59.00 | 7.59 | 22.93 |
| Found | 58.74 | 7.47 | 22.75 |

WORKING EXAMPLE 63

6,8-Diisobutyl-1-propionyl-2,3-dihydro-1H-imidazo[2',1':5,1]pyrazolo[3,4-d]pyrimidine-7,9(6H.8H)-dione A solution of 6,8-diisobutyl-2,3-dihydro-1H-imidazo[2',1':5,1]pyrazolo[3,4-d]pyrimidine-7,9(6H,8H)-dione (2 g) and propionic anhydride (2 ml) in pyridine (20 ml) was stirred at 50°–60° C. for 18 hr. The reaction mixture was concentrated to dryness to give a syrup. The syrup was purified by flash chromatography (silica gel, hexane/ethylacetate) to give a pale yellow syrup. Crystallization from n-hexane gave colorless crystals (1,4 g, 60%), m.p. 122°–123° C.

| Elemental Analysis for $C_{18}H_{27}N_5O_3$ | | | |
|---|---|---|---|
| | C (%) | H (%) | N (%) |
| Calcd. | 59.82 | 7.53 | 19.38 |
| Found | 59.68 | 7.48 | 19.18 |

WORKING EXAMPLE 64

6,8-Diisobutyl-1H-imidazo[2',1':5,1]pyrazolo[3,4-d]pyrimidine-7,9(6H,8H)-dione.

A solution of 6,8-diisobutyl-2,3-dihydro-1H-imidazo[2',1':5,1]pyrazolo[3,4-d]pyrimidine-4,6(5H,7H)-dione (20 g) and benzoyl peroxide (1.6 g) in chloroform (150 ml) was heated at reflux for 16 hr. The reaction mixture was concentrated to dryness and the resulting residue was taken up in chloroform, followed by washing with aqueous solution of sodium carbonate. The organic layer was dried and concentrated to dryness and the resulting crystals were recrystallized from methylene chloride/ethylacetate to give colorless crystals (9.1 g, 46%), m.p. 310°–311° C.

| Elemental Analysis for $C_{15}H_{21}N_5O_2$ | | | |
|---|---|---|---|
| | C (%) | H (%) | N (%) |
| Calcd. | 59.39 | 6,98 | 23.09 |
| Found | 59.24 | 6,92 | 22.80 |

EXAMPLES OF PHARMACEUTICAL PREPARATIONS

When a compound(I) of the present invention is intended for use as a therapeutic agent of chronic rheumatoid arthritis, lumbago, neck-shoulder-arm syndrome, liver disease or psoriasis, etc., the compound can be formulated into, for example, tablets or capsules having the following prescriptions.

| 1. Tablet | |
|---|---|
| (1) 6-Butyl-8-propyl-2,3-dihydro-1H-imidazo[2',1'5,1]pyrazolo-[3,4-d]pyrimidine-7,9(6H,8H)-dione | 10 mg |
| (2) Lactose | 35 mg |
| (3) Corn starch | 150 mg |
| (4) Microcrystalline cellulose | 30 mg |
| (5) Magnesium stearate | 5 mg |
| | 230 mg |

The whole amount each of (1), (2) and (3), together with two thirds of the amount of (4) and a half of the amount of (5), are mixed and then granulated. The residual amounts of (4) and (5) are added to the granules and compressed into a tablet.

| 2. Capsule | |
|---|---|
| (1) 6,8-Dibutyl-2,3-dihydro-1H-imidazo[2',1'5,1]pyrazolo-[3,4-d]pyrimidine-7,9(6H,8H)-dione | 10 mg |
| (2) Lactose | 100 mg |
| (3) Microcrystalline cellulose | 70 mg |
| (4) Magnesium stearate | 10 mg |
| | 190 mg |

The whole amount each of (1), (2) and (3), together with a half of the amount of (4), are mixed and then granulated. The residual amount of (4) is added to the granules, and the mixture is filled into a gelatine capsule.

| 3. Ointment (a) | |
|---|---|
| (1) 6-Pentyl-8-propyl-2,3-dihydro-1H-imidazo[2',1':5,1]pyrazolo[3,4-d]-pyrimidine-7,9(6H,8H)-dione | 2.5 g |
| (2) Macrogol 400 | 70.0 g |
| (3) Macrogol 4000 | 27.5 g |
| | 100.0 g |

(1) was dissolved in the mixture of (2) and (3) by warming and the resulting solution was cooled gradually under stirring into an ointment.

| 4. Ointment (b) | |
|---|---|
| (1) 6,8-dipropyl-1H-imidazo[2',1':5,1]pyrazolo[3,4-d]-pyrimidine-7,9(6H,8H)-dione | 1.25 g |
| (2) white soft paraffine | 98.75 g |
| | 100.00 g |

(1) was dissolved in (2) by warming and the resulting solution was cooled gradually under stirring into an ointment.

EXPERIMENTAL EXAMPLE 1

(1) Antiinflammatory action (Carrageenin edema method)

Using a group of six Jcl: SD rats (6 week old, male), antiinflammatory action was investigated in accordance with the method of Winter et al. [Proc. Soc. Exp. Biol. Med., 111, 544(1962)]. One hour after the oral administration of 50 mg/kg of a test sample, the animals were injected subcutaneously with 0.05 ml each of a 1% solution of carrageenin in physiological saline solution into a sole. The volume of the hind-paw was measured 3 hours later and compared with that before the injection, and the edema volume was determined from the difference. By comparing the edema volumes of animal groups untreated and treated with test samples, the inhibition rate was determined. The results are shown in Table 1.

(2) Antiinflammatory action (Reversed passive Arthus reaction)

A group consisting of six Jcl: SD rats (7 week old, male was used. The hair of the back of the animals was cut, under ether anesthesia, and 1 ml each of a 0.5% solution of egg albumin in physiological saline solution was injected into the tail vein of each test animal, followed by intradermal injection of 0.1 ml of rabbit anti-egg albumin antiserum at each side of the left and right of the back and a further intradermal injection of 0.1 ml of physiological saline solution at the left side. Three hours later, each animal was intravenously injected with 1 ml of 1% Evans' blue physiological saline solution. Thirty minutes later, the test animals were exfoliated and the area(mm$^2$) of each of the blue spot was measured. The test sample in a dose of 12.5 mg/kg was orally administered one hour before the injection of egg albumin. By comparing the area(mm$^2$) of the blue spot in the test group with that of the control group, inhibition rate was determined. The results are shown in Table 1.

EXPERIMENTAL EXAMPLE 2

Analgesic action (Phenyl quinone writhing method)

Using a group of 10 Slc: ICR mice (4 week old, male), analgesic action was investigated in accordance with the method of Siegmund et al. [Proc. Soc. Exp. Biol. Med., 95, 729(1957)]. A test sample in a dose of 50 mg/kg was orally administered, and 30 minutes later, a 0.02% aqueous phenyl quinone solution was intraperitoneally injected in the proportion of 0.1 ml relative to 10 g of body weight. Over the period of 20 minutes from the injection, the number of writhings was counted for the individual animals. By comparing the untreated and treated animal groups for the number of reactions, the writhing inhibition rate was determined. The results are shown in Table 1.

TABLE I

Analgesic and antiinflammatory action of compound (I)

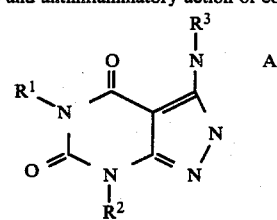

| Compound (I) | | | | | Inhibition rate (%) | | |
|---|---|---|---|---|---|---|---|
| Working Example No. | $R^1$ | $R^2$ | $R^3$ | A | Reversed passive Arthus reaction | Carrageenin edema | Phenyl quinone writhing |
| 29 | All | All | H | CH$_2$CH$_2$ | 73*** | 79** | 80**(a) |
| 45 | All | All | H | CH=CH | 74*** | 85*** | 87** |
| 13 | Pr | Pr | H | CH$_2$CH$_2$ | 65** | 97** | 95*** |
| 44 | Pr | Pr | H | CH=CH | 91*** | 90** | 96*** |
| 33 | Pr | Pr | COEt | CH$_2$CH$_2$ | 87** | 87** | 77** |
| 18 | Pr | All | H | CH$_2$CH$_2$ | 87** | 93** | 90** |
| 49 | Pr | All | H | CH=CH | 88*** | 80** | 80*** |
| 43 | Pr | Bu | H | CH=CH | 90** | 109** | 89*** |
| 40 | Pr | Bu | Ac | CH$_2$CH$_2$ | 69** | 82** | 89*** |
| 48 | Pr | i-Bu | H | CH=CH | 93*** | 95** | 91** |
| 6 | Pr | Pen | H | CH$_2$CH$_2$ | 71*** | 105** | 96*** |
| 50 | Pr | Pen | H | CH=CH | 79** | 78** | 89*** |
| 17 | Pr | i-Pen | H | CH$_2$CH$_2$ | 73** | 83** | 79** |
| 46 | Bu | Bu | H | CH=CH | 70*** | 90*** | 96*** |
| 7 | Et | Et | H | CH$_2$CH$_2$ | 42** | 99** | 52** |
| 10 | Pr | Et | H | CH$_2$CH$_2$ | 36** | 100** | 87** |
| 2 | Pr | Bu | H | CH$_2$CH$_2$ | 65*** | 103** | 100*** |
| 3 | Bu | Bu | H | CH$_2$CH$_2$ | 68** | 100** | 98** |
| 1 | Pr | Bu | Me | CH$_2$CH$_2$ | 32* | 70** | 97*** |

TABLE I-continued

Analgesic and antiinflammatory action of compound (I)

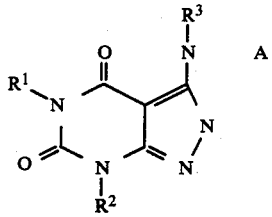

| Compound (I) | | | | | Inhibition rate (%) | | |
|---|---|---|---|---|---|---|---|
| Working Example No. | $R^1$ | $R^2$ | $R^3$ | A | Reversed passive Arthus reaction | Carrageenin edema | Phenyl quinone writhing |
| 23 | Pr | Bu | Ac | $CH_2CH_2$ | 69*** | 82** | 89*** |

(a)*Statistically significant difference (P < 0.05)
**Statistically significant difference (P < 0.01)
***Statistically significant difference (P < 0.001)

EXPERIMENTAL EXAMPLE 3

A group of 10 BALB/c mice (7 week old, male) was used. Each mouse was injected into the tail vein with *P. acnes* killed by heating at a dose of 1 mg/mouse. Seven days later, each mouse was injected intravenously with LPS(1 1 μg/mouse) derived from *Salmonella enteritidis* to cause acute hepatic failure. Usually, in a group of mice intravenously injected with LPS, 90% to 100% of the animals die within 24 hours. Using this model, each compound was tested. Each compound(I) shown in Table 2 was suspended in a 5% gum arabic vehicle and was orally administered to the animals at 0.3 mg/kg one hour prior to the injection of LPS, and then 48 hours later, the number of the dead mice was determined. The mice in the control group were orally given the 5% gum arabic vehicle one hour prior to LPS administration. The results are shown in Table 2.

As shown in the Table 2, the compound (I) significantly protected the mice from lethality by acute hepatic failure.

TABLE 2

Effect of compound (I) against acute heptatic failure due to *P. Acness*-LPS

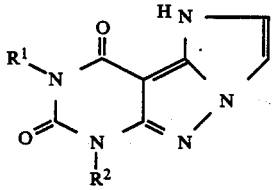

| Compound (I) | | | Anti-lethal effect: Number of dead mice (effective ratio %) | |
|---|---|---|---|---|
| Working Example No. | $R^1$ | $R^2$ | Control(a) | Compound (0.3 mg/kg,p.o.) |
| 45 | All | All | 10 | 0(100**(b)) |
| 44 | Pr | Pr | 10 | 0(100*) |
| 49 | Pr | All | 10 | 3(70**) |
| 43 | Pr | Bu | 10 | 0(100**) |
| 48 | Pr | i-Bu | 10 | 1(90**) |
| 50 | Pr | Pen | 10 | 1(90**) |
| 46 | Bu | Bu | 10 | 2(80**) |

(a)Animals in Control Group were administered with only a 5% gum arabic vehicle
(b)** shows statistically significant difference (P 21 0.1)

EXPERIMENTAL EXAMPLE 4

A group of 5 Jcl: Wistar rats (5 week old, 90–110 g body weight, Japan Clea, male) and a group of 5 Jcl: ICR mice (5 week old, 25–30 g body weight, Japan Clea, male) were used. These rats were each administerred orally with 10 ml/kg of the test compound (250 mg/kg), while these mice were each administered orally with 20 ml/kg of the test compound (500 mg/kg).

These oral administrations were made on the form of a suspension in 5% gum arabic vehicle. One week later, the number of dead animals was observed. The results are shown in Table 3.

TABLE 3

| Working Example No. | Mice (500 mg/kg,p.o.) | Rats (250 mg/kg,p.o.) |
|---|---|---|
| 13 | 0 | 0 |
| 40 | 0 | 0 |

What is claimed is:

1. A compound of the formula:

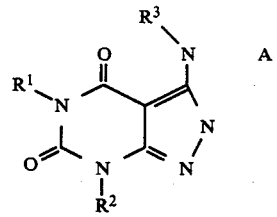

wherein
$R^1$ and $R^2$ are independently $C_{1-8}$ alkyl or $C_{2-8}$ alkenyl; $R^3$ is hydrogen, $C_{1-3}$ alkyl, $C_{2-3}$ alkenyl, $C_{1-6}$ alkyl-CO-, benzoyl, $C_{1-4}$ alkyl-O-CO-, carbamoyl or formyl; and A is $C_{2-4}$ alkylene or $C_{2-4}$ alkenylene which may be substituted with $C_{1-3}$ alkyl, halogen, nitro, amino, oxo, unsubstituted phenyl or phenyl substituted with 1 to 2 members selected from the class consisting of amino, nitro, hydroxy, methoxy and methyl, and a salt thereof.

2. A compound according to claim 1, wherein $R^1$ and $R^2$ are independently $C_{2-5}$ alkyl or $C_{2-5}$ alkenyl.

3. A compound according to claim 1, wherein $R^1$ and $R^2$ are independently $C_{2-5}$ alkyl.

4. A compound according to claim 1, wherein $R^3$ is hydrogen, $C_{1-3}$ alkyl, $C_{1-6}$ alkyl-CO- or $C_{1-4}$ alkyl-O-CO-.

5. A compound according to claim 1, wherein $R^3$ is hydrogen.

6. A compound according to claim 1, wherein A is a hydrocarbon chain represented by the formula:

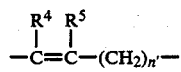

wherein
R$^4$ and R$^5$ are independently hydrogen, C$_{1-3}$ alkyl, or phenyl optionally substituted with 1 to 2 members selected from the class consisting of amino, nitro, hydroxy, methoxy and methyl; and
n′ is an integer of 0 to 2, or
a hydrocarbon chain represented by the formula:

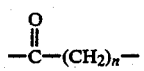

wherein n is an integer of 1 to 3.

7. A compound according to claim 1, wherein A is a hydrocarbon chain represented by the formula:

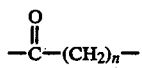

wherein n is an integer of 1 to 3.

8. A compound according to claim 1, wherein A is a hydrocarbon chain represented by the formula:

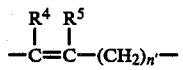

wherein R4 and R5 are independently hydrogen, C$_{1-3}$ alkyl, or phenyl optionally substituted with 1 to 2 members selected from the class consisting of amino, nitro, hydroxy, methoxy and methyl; and n′ is an integer of 0 to 2.

9. A compound according to claim 1, wherein A is ethylene or vinylene.

10. A compound according to claim 1, wherein A is vinylene and R$^3$ is hydrogen.

11. A compound according to claim 1, wherein R$^1$ and R$^2$ are independently C$_{3-5}$ alkyl;
R$^3$ is hydrogen, acetyl, propionyl or methoxycarbonyl; and
A is ethylene or vinylene, or
a pharmacologically acceptable salt thereof.

12. A pharmacologically acceptable salt according to claim 1, which is a pharmacologically acceptable acid addition salt.

13. A compound according to claim 1, which is 6-butyl-8-propyl-1H-imidazo[2′,1′:5,1]pyrazolo[3,4-d]pyrimidine-7,9(6H,8H)-dione.

14. A compound according to claim 1, which is 6-pentyl-8-propyl-2,3-dihydro-1H-imidazo[2′,1′:5,1-]pyrazolo[3,4-d]pyrimidine-7,9(6H,8H)-dione.

15. A compound according to claim 1, which is 6,8-diisobutyl-1-methyl-2,3-dihydro-1H-imidazo[2′,1′:5,1-]pyrazolo[3,4-d]pyrimidine-7,9(6H,8H)-dione.

16. A compound according to claim 1, which is 6,8-diallyl-1-propionyl-2,3-dihydro-1H-imidazo[2′,1′:5,1-]pyrazolo[3,4-pyrimidine-7,9(6H,8H)-dione.

17. A compound according to claim 1, which is 6,8-dipropyl-1H-imidazo[2′,1′:5,1]pyrazolo[3,4-d]pyrimidine-7,9(6H,8H)-dione.

18. A compound according to claim 1, which is 6,8-dibutyl-1H-imidazo[2′,1′:5,1]pyrazolo[3,4-d]pyrimidine-7,9(6H,8H,)-dione.

19. A pharmaceutical composition suitable for an antiinflammatory, analgesic, antipyretic, anti-allergic or liver-protecting agent which comprises
(a) as the active ingredient, an effective amount of a compound as claimed in claim 1 and
(b) a pharmacologically acceptable carrier, excipient or diluent therefor.

20. A liver-protecting pharmaceutical composition according to claim 19, containing an effective liver-protecting amount of the said active ingredient.

21. A method for treatment or amelioration of chronic rheumatoid arthritis, lumbago, or neck-shoulder-arm syndrome in a mammal, which comprises administering to said mammal an effective amount of a compound as claimed in claim 1.

22. A method for treatment or prevention of hepatic injury in a mammal, which comprises administering to said mammal an effective amount of a compound as claimed in claim 1.

* * * * *

UNITED STATES PATENT AND TRADEMARK OFFICE
CERTIFICATE OF CORRECTION

PATENT NO. : 4,912,104

DATED : March 27, 1990

INVENTOR(S) : Takehiko NAKA et al.

It is certified that error appears in the above-identified patent and that said Letters Patent is hereby corrected as shown below:

In the abstract, and Columns 1, 44, 45 and 46,

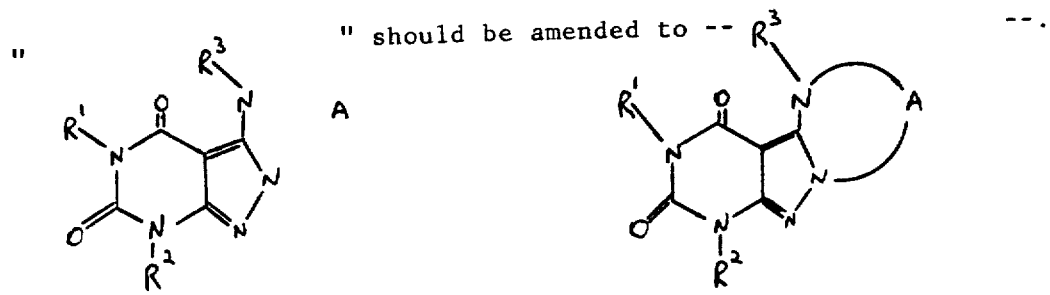

Column 1, last line, "carbamoy" should be amended to --carbamoyl--.

Column 2, lines 47-67, the reaction scheme of <u>Reaction(a)</u> should be deleted and inserted into lines 20-25 of Column 3.

Column 3, lines 20-25, "(-C(=O)-CH$_2$-)," should be deleted.

This certificate supersedes Certificate of Correction issued October 22, 1991.

Signed and Sealed this

Twenty-fifth Day of February, 1992

Attest:

HARRY F. MANBECK, JR.

Attesting Officer

Commissioner of Patents and Trademarks